(12) United States Patent
Shroff et al.

(10) Patent No.: US 10,520,714 B2
(45) Date of Patent: Dec. 31, 2019

(54) SYSTEMS AND METHODS FOR INSTANT TOTAL INTERNAL REFLECTION FLUORESCENCE/ STRUCTURED ILLUMINATION MICROSCOPY

(71) Applicant: The USA, as represented by the Secretary, Dept. of Health and Human Services, Bethesda, MD (US)

(72) Inventors: Hari Shroff, Bethesda, MD (US); Justin Taraska, Bethesda, MD (US); John Giannini, Bethesda, MD (US); Yicong Wu, Bethesda, MD (US); Abhishek Kumar, Bethesda, MD (US); Min Guo, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/326,757

(22) PCT Filed: Aug. 23, 2017

(86) PCT No.: PCT/US2017/048234
§ 371 (c)(1),
(2) Date: Feb. 20, 2019

(87) PCT Pub. No.: WO2018/039361
PCT Pub. Date: Mar. 1, 2018

(65) Prior Publication Data
US 2019/0179128 A1    Jun. 13, 2019

Related U.S. Application Data

(60) Provisional application No. 62/378,307, filed on Aug. 23, 2016.

(51) Int. Cl.
G02B 21/16 (2006.01)
G02B 21/00 (2006.01)
G01N 21/64 (2006.01)
G02B 27/58 (2006.01)
G02B 21/36 (2006.01)

(52) U.S. Cl.
CPC ........... *G02B 21/16* (2013.01); *G01N 21/648* (2013.01); *G01N 21/6458* (2013.01);
(Continued)

(58) Field of Classification Search
CPC ........ G02B 21/16; G02B 27/58; G02B 21/36; G02B 21/0032; G02B 21/0076;
(Continued)

(56) References Cited

U.S. PATENT DOCUMENTS 9,360,660 B2   6/2016   Yi et al.
2016/0238827 A1   8/2016   Shroff et al.

FOREIGN PATENT DOCUMENTS

WO    2012/118530 A1    9/2012

OTHER PUBLICATIONS

PCT/US17/48234—International Search Report and Written Opinion—dated Nov. 3, 2017.
(Continued)

*Primary Examiner* — David P Porta
*Assistant Examiner* — Gisselle M Gutierrez
(74) *Attorney, Agent, or Firm* — Polsinelli PC

(57) ABSTRACT

Embodiments related to systems and methods for instant structured microscopy where total internal reflection fluorescence techniques are used to improve optical sectioning and signal-to-noise ratio of structured illumination microscopy are disclosed.

20 Claims, 18 Drawing Sheets

(52) U.S. Cl.
CPC ..... *G02B 21/0032* (2013.01); *G02B 21/0044* (2013.01); *G02B 21/0076* (2013.01); *G02B 21/36* (2013.01); *G02B 27/58* (2013.01); *G01N 2021/6463* (2013.01); *G01N 2201/105* (2013.01); *G02B 21/0048* (2013.01)

(58) Field of Classification Search
CPC ............ G02B 21/0044; G02B 21/0048; G01N 21/6458; G01N 21/648; G01N 2201/105; G01N 2021/6463
USPC .......................................... 250/458.1, 459.1
See application file for complete search history.

(56) References Cited

OTHER PUBLICATIONS

Bai et al, Synthesis of Superparamagnetic nanotubes as MRI contrast agents and for cell labeling, Nanomedicine, pp. 163-174, 2008, vol. 3, No. 2.

Lanaz et al, 1H/19F Magnetic Resonance Molecular Imaging with Perfluorocarbon Nanoparticles, Current Topics in Developmental Biology, 2005, pp. 57-76, vol. 70.

Seevinck et al, Factors Affecting the Sensitivity and Detection Limits of MRI, CT, and SPECT for Multimodal Diagnostic and Therapeutic Agents. Anti-Cancer Agents in Medicinal Chemistry, 2007, pp. 317-334, vol. 7.

Sitharaman et al, Superparamagnetic Gadonanotubes are High-Performance MRI contrast agents. Chem. Commun., 2005, pp. 3915-3917.

Sukstanskii et al, Theroy of FID NMR Signal Dephasing Induced by Mesoscopic Magnetic Field Inhomogeneities in Biological Systems, Journal of Magnetic Resonance, 2001, pp. 107-117, vol. 151.

Woods et al, Paramagnetic Lanthanide Complexes as PARACEST Agents for Medical Imaging, Chemical Society Reviews, 2006, vol. 35.

Zabow et al, Design and Fabrication of a Micromachined Multispectral Magnetic Resonance Imaging Agent. J. Micromech. Microeng., 2009, pp. 1-10, vol. 19.

Zabow et al, Micro-Engineered Local Field Control for High=Sensitivity Multispectral MRI. Nature, 2008, pp. 1058-1064, vol. 453 No. 19.

SYSTEMS AND METHODS FOR INSTANT TOTAL INTERNAL REFLECTION FLUORESCENCE/ STRUCTURED ILLUMINATION MICROSCOPY

FIELD

The present disclosure generally relates to instant structured illumination microscopy (SIM) and in particular to systems and methods for instant structured illumination microscopy where total internal reflection fluorescence (TIRF) techniques may be used to improve optical sectioning and signal-to-noise ratio.

BACKGROUND

Total internal reflection occurs when highly inclined light impinges upon a refractive index boundary (with first medium index $n_1$ and second medium index $n_2$, with $n_1 > n_2$). According to Snell's Law, $n_1 \sin(\theta 1) = n_2 \sin(\theta 2)$, where theta1 is the angle of incoming light (measured from the surface normal) and theta2 is the corresponding outgoing angle for the refracted light. For theta2=pi/2, theta1=arc sin($n_2/n_1$) is the "critical angle". Any light ray at or exceeding the critical angle is "totally internally reflected", and no light propagates past the interface into the far field on the lower index side of the boundary. Nevertheless, an evanescent wave exists at the interface of the boundary and can excite fluorescent molecules within lambda (the wavelength of excitation) distance from the boundary, on the $n_2$ side. This evanescent wave is used in TIRF to generate very high contrast, high signal-to-noise ratio images of fluorescently-labeled samples, such as the cell membrane, at or near the coverslip boundary.

A convenient method of setting up TIRF conditions is to use a high numerical aperture objective (typically 1.4 NA or higher, so that aqueous samples with n2~1.33, the refractive index of a cell may be imaged) and ensure that only marginal rays pass through the back focal plane of the objective lens. Such "objective side TIRF" has been very successful in cell biology applications, where it has been used for decades.

Structured illumination microscopy (SIM) is a method that uses sharply patterned light and post-processing of images to enhance image resolution (in its linear form, doubling resolution). In traditional SIM, a series of images are acquired with a camera and computationally processed to improve resolution. This implementation of SIM has also been combined with TIRF, but the implementation still requires 9 raw images relative to normal TIRF microscopy, thereby slowing acquisition 9-fold relative to conventional, diffraction-limited imaging. As such, there is a need for a method that combines SIM with TIRF conditions that does not result in a loss of speed relative to conventional TIRF microscopy.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
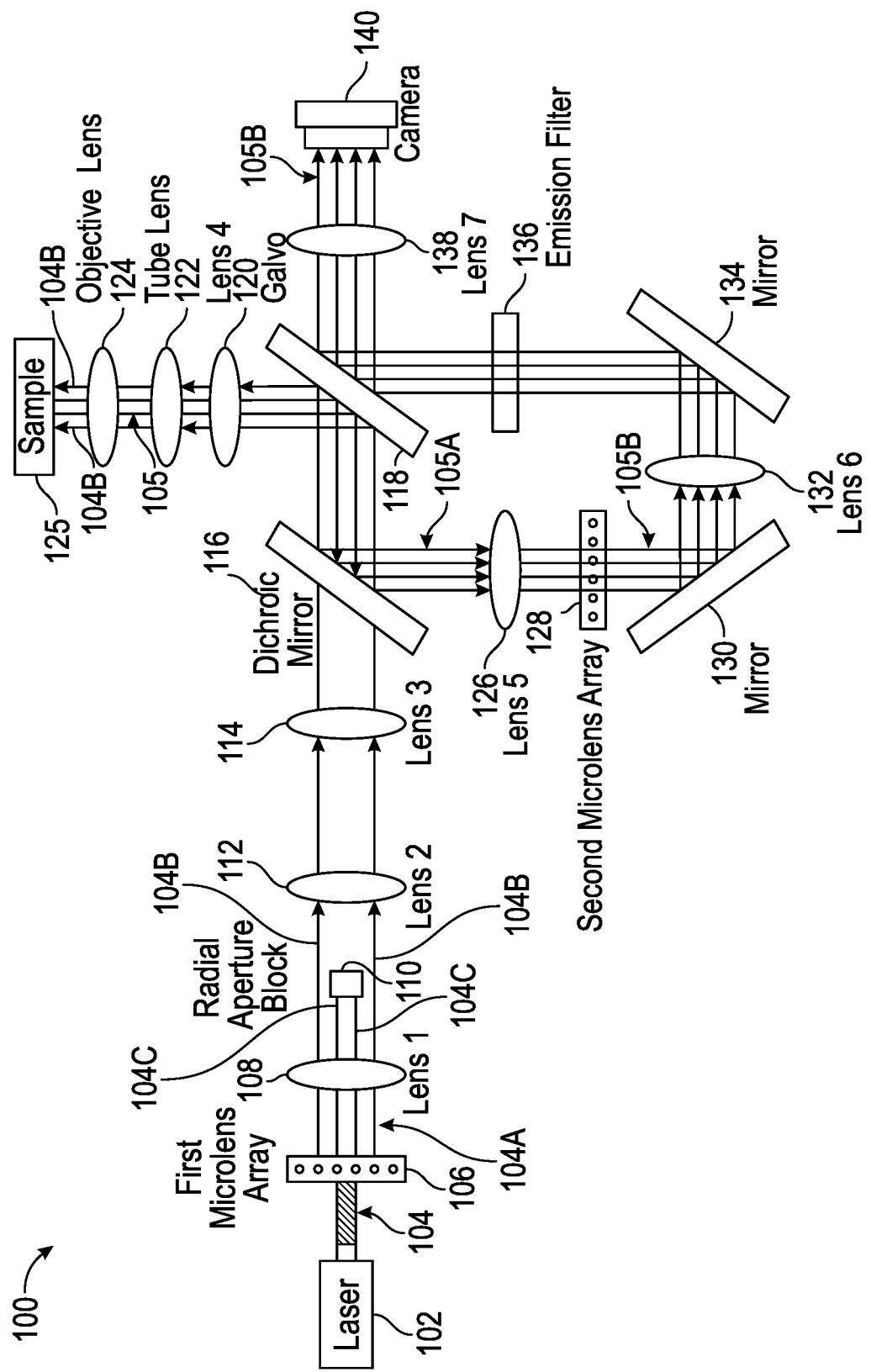
FIG. 1 is a simplified illustration showing a first embodiment of an instant TIRF/SIM system with a radial aperture block, according to aspects of the present disclosure.

Systems and methods for applying total internal reflection fluorescence (TIRF) to instant structured illumination microscopy (SIM) are disclosed herein. In some embodiments, the instant TIRF/SIM system includes a radial aperture block positioned at a plane conjugate to the back focal plane of the objective lens, thus allowing only high-angle marginal annular light beams from a laser source to excite the sample. In some embodiments, the radial aperture block of the first embodiment of the instant TIRF/SIM system is replaced with a digital micromirror device (DMD) for varying the evanescent wave to allow ~nm localization of features in the axial direction. In some embodiments, a spatial light modulator (SLM) is used to alter the phase of the excitation to optimally induce evanescent, patterned excitation at the sample. In some embodiments, the radial aperture block is combined with a spinning disk arrangement including a pair of spinning disks having converging microlenses which are arranged with a spinning disk having pinholes to produce contracted non-inverted images of fluorescent foci being emitted by the sample. Combinations of the SLM, DMD, spinning disk arrangement, and an aperture block are also possible. Various embodiments of the instant TIRF/SIM system allows for high-speed, super-resolution microscopy at very high signal-to-noise (SNR) ratios for biological applications within ~200 nm (e.g., the evanescent wave decay length) distance of a coverslip surface. Referring to the drawings, embodiments of an instant TIRF/SIM system are illustrated and generally indicated as 100, 200, 300 and 400 in FIGS. 1-19.

Referring to FIG. 1, a first embodiment of the instant TIRF/SIM system, designated 100 implements a radial aperture block 110 positioned at a plane conjugate to the back focal plane of the objective lens 124, thus allowing only marginal, annular excitation light beams to pass through for scanning onto a sample 125 as shown in FIG. 1. In this embodiment, the instant TIRF/SIM system 100 includes an excitation source 102, for example a laser component, that generates an excitation beam 104 which is transmitted through a first micro lens array 106. The first micro lens array 106 splits the excitation beam 104 into an array of excitation foci 104A. A first lens 108 is positioned one focal length away from the focal point of the first micro lens array 106. In addition, a radial aperture block 110 is positioned at the front focal plane of the first lens 108 to block central rays emerging from the first lens 108, thereby allowing only high-angle, marginal rays 104B emerging from the first lens 108 to pass through the radial aperture block 110.

An imaging telescope arrangement includes a second lens 112 in line with a third lens 114 that collectively image the marginal rays 104B that pass through the radial aperture block 110. The second and third lenses 112 and 114 image the marginal rays 104B to pass through a dichroic mirror 116 and onto a two-sided galvanometric mirror 118. In some embodiments, the second and third lenses 112 and 114 are separated by the sum of their respective focal lengths. The galvanometric mirror 118 redirects and scans the marginal rays 104B through a fourth lens 120 in line with a tube lens 122 and onto the back focal plane of a high numerical aperture objective lens 124. This optical arrangement produces a structured illumination that does not propagate into the sample 125, but evanescently excites the sample 125 with the marginal rays 104B being imaged onto the sample 125 by the objective lens 124. Since the marginal rays impinge upon the sample at an angle that exceeds the critical angle they do not propagate into the sample, instead causing only an evanescent wave that decays exponentially within the sample. The combination of evanescent (caused by the high angle rays that are created by the radial annular block 110), patterned/structured illumination (caused by the micro lens array 106) causes very sharp/high contrast excitation at the sample. In some embodiments, the objective lens 124 may have a numerical aperture >1.4 NA (i.e. greater than the refractive index of the sample 125), such as 1.65 NA or 1.70 NA.

The resulting excitation 105 generated by the sample 125 scanned by the galvanometer mirror 118 produces a patterned fluorescence emission 105A that may be collected in epi-mode, and then descanned by the galvanometric mirror 118 as the fluorescence emissions 105A are imaged by the arrangement of the objective lens 124, tube lens 122 and fourth lens 120 aligned with the galvanometric mirror 118. The fluorescence emissions 105A emitted by the sample 125 are then separated from the resulting excitation 105 via the dichroic mirror 116 that redirects the fluorescence emission 105A.

Figure 18:
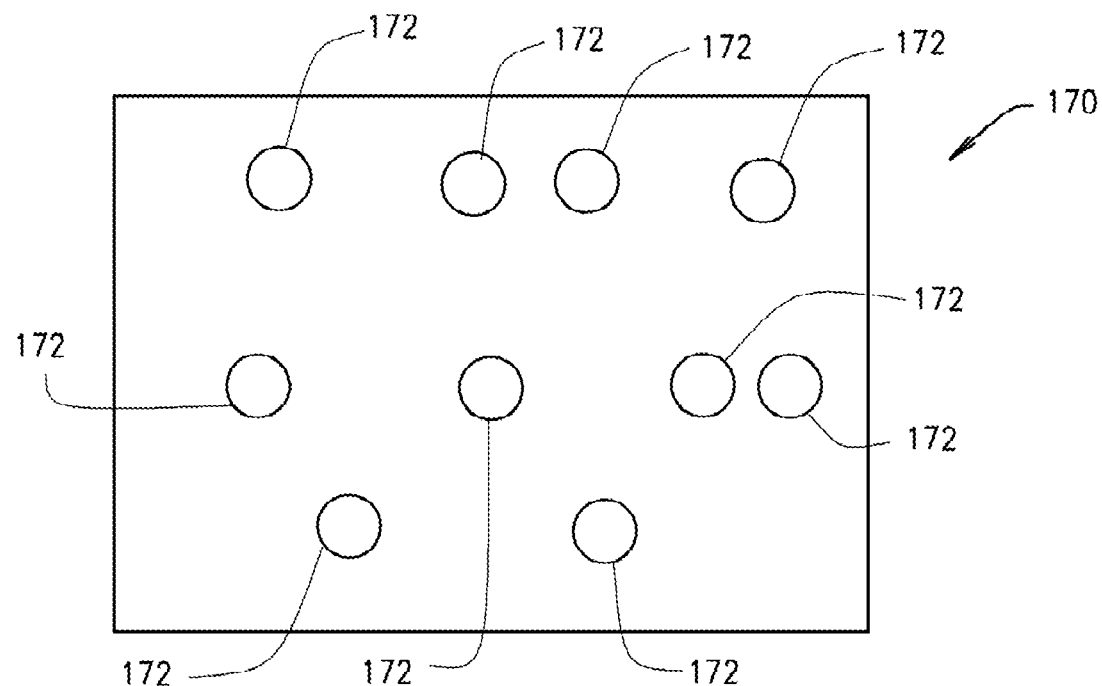
FIG. 18 is a simplified illustration showing a multi-focal pattern with a plurality of focal points.
Figure 19:
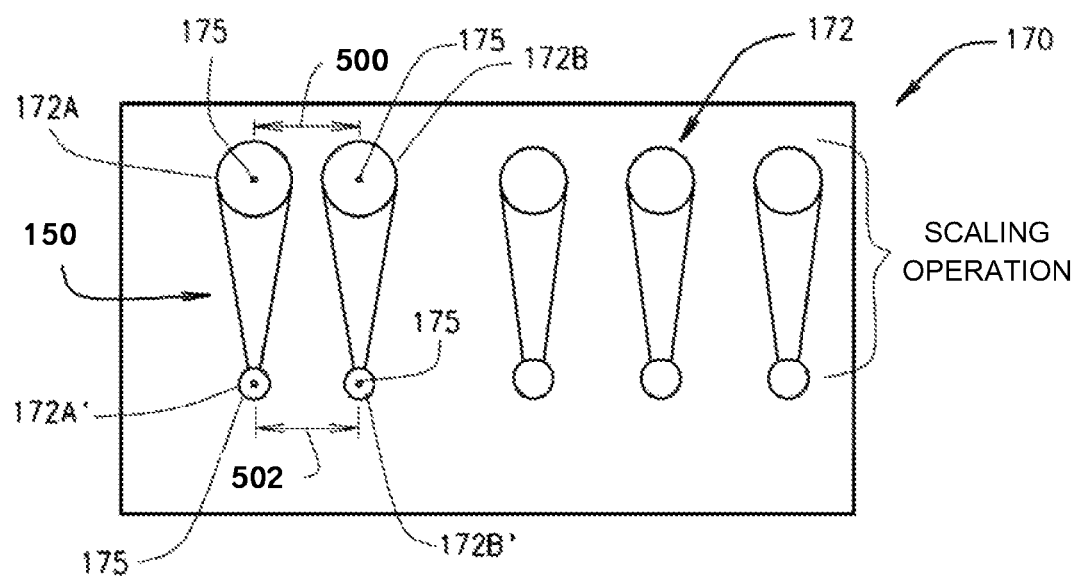
FIG. 19 is a simplified illustration showing a scaling operation that scales in-focus fluorescent emissions resulting from a multi-focal fluorescence pattern emitted by a sample.

In some embodiments, a fifth lens 126 is positioned one focal length from the galvanometric mirror 118. The fifth lens 126 focuses the descanned fluorescence emission 105A through a second micro lens array 128. In some embodiments, the second micro lens array 128 has the same pitch/pattern and lens spacing as the first micro lens array 106 such that the fluorescence emissions 105A are locally contracted into contracted fluorescence emissions 105G without inversion or changing the relative distance between adjacent fluorescence emissions 105A as shown in FIGS. 18 and 19.

When the contracted fluorescence emissions 105G are locally contracted the "contraction factor" depends on the respective wavelengths of the excitation beam 104 and fluorescence emissions 105A and the properties of the radial aperture block 110, and in most cases, may be set at a value of approximately 2. For example, a multi-focal pattern 170 for the fluorescence emissions 105A that may be locally contracted into contracted fluorescence emissions 105G is shown in FIGS. 18 and 19. In one embodiment, the multi-focal pattern 170 may include a plurality of focal points 172 arranged in a particular multi-focal pattern 170 defined by the plurality of light beams with each multi-focal pattern 170 defining a different arrangement of focal points for the plurality of light beams such that multi-focal pattern 170 maximizes the distance between any two nearest focal points 172 for a given density of focal points 172, thereby minimizing crosstalk. As used herein, the term "crosstalk" refers to the ability of nearby light beams to cause excitation and fluorescence from other focal points to appear as if focal points originate from the focal point in question. In a scanning operation, the plurality of light beams in each multi-focal illumination pattern are rastered onto the sample 125 being illuminated such that the sample 125 emits a plurality of fluorescent emissions. The fluorescent emissions emitted by the sample 125 are rastered in a de-scanning operation which redirects the plurality of fluorescent emissions for removal of out-of-focus fluorescent emissions in a focusing operation. In the focusing operation, out-of-focus fluorescent emissions are blocked and only in-focus fluorescent emissions are allowed to pass through for processing.

The in-focus fluorescent emissions caused by each multi-focal pattern are then scaled using a scaling operation that locally contracts each of fluorescent emissions by a predetermined factor. In one embodiment of the scaling operation illustrated in FIG. 19, a local contraction of the fluorescent foci 172 caused in a single multi-focal pattern 170 occurs. For example, the local contraction of fluorescent foci 172A and 1726 to scaled fluorescent foci 172A' and 1726', respectively, in the multi-focal pattern 170 is such that the distance 500 between the geometric centers 175 of fluorescent foci 172A and 1726 and the distance 502 of fluorescent foci 172A and 172B remains the same regardless of the degree of scaling applied to the fluorescent foci 172 of the multi-focal pattern 170. In other words, the scaling operation 150 contracts the fluorescent foci 172 locally while keeping the relative distances between each of the fluorescent foci the same.

Referring back to FIG. 1, in some embodiments, a sixth lens 132 is positioned between opposing first and second mirrors 130 and 134. The sixth lens 132 is positioned one focal length from the contracted fluorescence emissions 105B and the galvanometer mirror 118 and serves to Fourier-transform the contracted fluorescence emissions 105B onto the galvanometer mirror 118. In this arrangement, the galvanometer mirror 118 and the seventh lens 138 serve to rescan the contracted fluorescence emissions 105B that forms an image onto a detector component 140, such as a camera, to capture the image.

In some embodiments, an emission filter 136 may be interposed between the second mirror 134 and the galvanometer 118 to remove any residual resulting excitation 105 from the contracted fluorescence emissions 105B.

Figure 2:
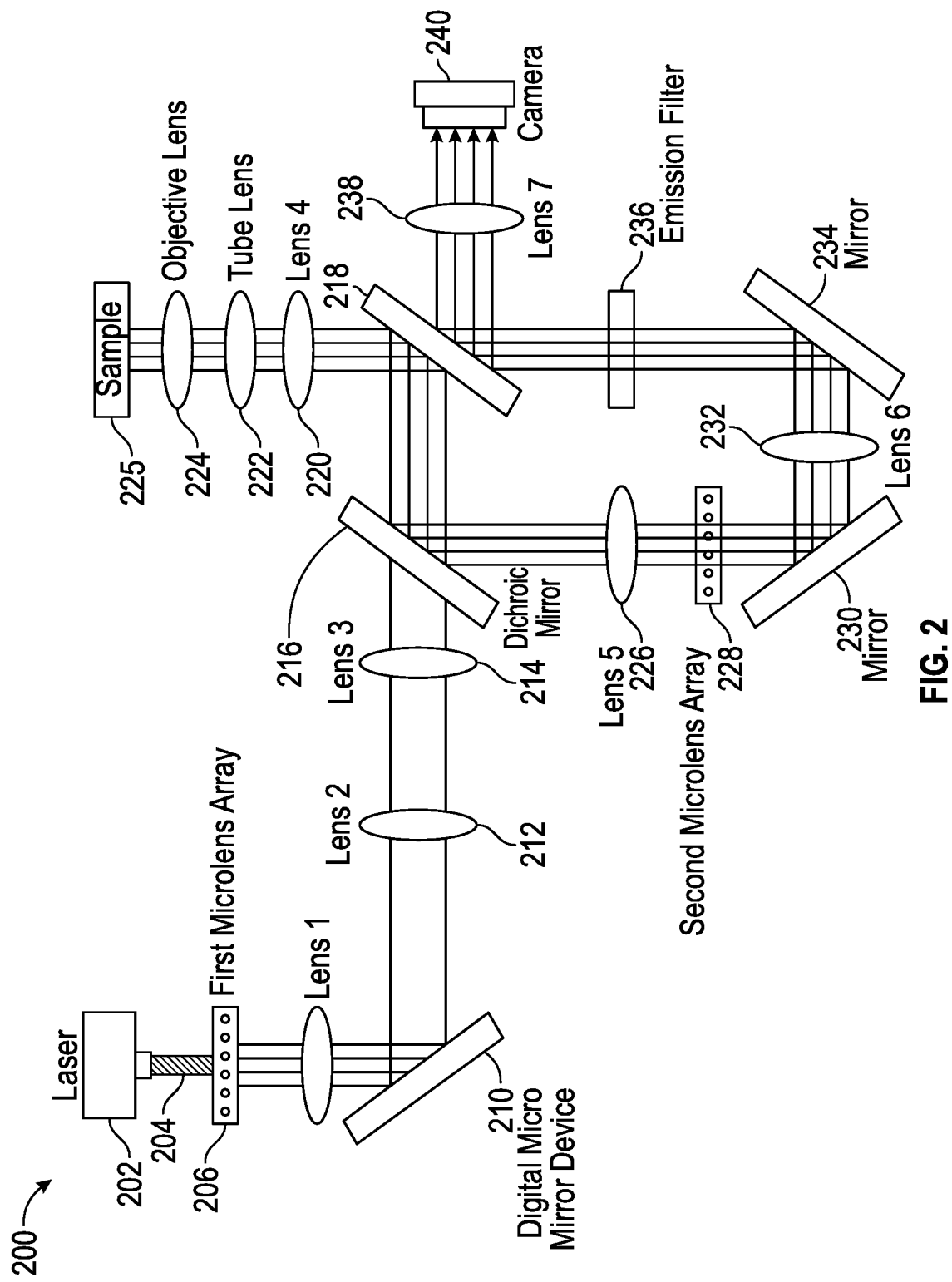
FIG. 2 is a simplified illustration showing a second embodiment of with an instant TIRF/SIM system with a digital micro-mirror device, according to aspects of the present disclosure.

Referring to FIG. 2, another embodiment of the instant TIRF/SIM system, designated 200, substitutes the radial aperture block 110 with a digital micromirror device 210 that varies the evanescent wave to allow ~nm localization of feature in the axial direction. In this embodiment, the instant TIRF/SIM system 200 includes an excitation source 202, for example a laser component, that generates an excitation beam 204 that is transmitted and passes through a first micro lens array 206. The first micro lens array 206 splits the excitation beam 204 into an array of excitation foci 204A. A first lens 208 is positioned one focal length away from the focal point of the first micro lens array 206. As noted above, the digital micromirror device 210, rather than a radial aperture block 110, may be in communication with the first microlens array 206. In some embodiments, the digital micromirror device 210 is positioned at the front focal plane of the first lens 208 to block all but the high-angle marginal rays 104B emerging from the first lens 208. In other words, all of the pixels of the digital micromirror device 210, except those pixels along the periphery of the digital micromirror device 210, are set to reflect the low-angle central rays off axis, thus effectively removing the low-angle central rays from illuminating the sample 225 in a manner similar to the radial block aperture 110. By varying the number and area of the pixels in this reflective zone, the degree of transmitted marginal rays 104B can also be varied, ultimately corresponding to varying the thickness of the evanescent field at the sample 225.

In some embodiments, an imaging telescope arrangement includes a second lens 212 in line with a third lens 214 that collectively image the marginal rays 204B to pass through a dichroic mirror 216 and onto a two-sided galvanometric mirror 218. In some embodiments, the second and third lenses 212 and 214 are separated by a distance that is the sum of their respective focal lengths. The galvanometric mirror 218 redirects and images the marginal rays 204B along third axis 404 through a fourth lens 220 in line with a tube lens 222 and onto the back focal plane of a high numerical aperture objective lens 224. This arrangement produces a structured illumination that does not propagate into a sample 225, but evanescently excites the sample 224 with the marginal rays 204B imaged onto the sample 225 by the objective lens 224. In some embodiments, the objective lens 224 may have a numerical aperture >1.4 NA, such as 1.65 NA or 1.70 NA.

The resulting excitation 205 of the sample 225 produces a patterned fluorescence emission 205A that may be collected in epi-mode, and then descanned by the galvanometric mirror 218 as the fluorescence emissions 205A are imaged by the objective lens 224, tube lens 222 and fourth lens 220 onto the galvanometer mirror 218. The fluorescence emissions 205A are then separated from the resulting excitation 205 via the dichroic mirror 216 that redirects the fluorescence emission 205A.

In some embodiments, a fifth lens 226 is positioned one focal length from the galvanometric mirror 218. The fifth lens 226 focuses the descanned fluorescence emission 205A through a second micro lens array 228. In some embodiments, the second micro lens array 228 has the same pitch/pattern and lens spacing as the first micro lens array 206 such that the fluorescence emissions 205A are locally contracted into contracted fluorescence emissions 205B without inversion or changing the relative distance between adjacent fluorescence emissions 205A.

When the contracted fluorescence emissions 205B are locally contracted the contraction factor depends on the respective wavelengths of the excitation beam 204 and fluorescence emissions 205A and the characteristics of the pattern displayed on the digital micro-mirror device 210 and as discussed above, may be set at a value of approximately 2. In some embodiments, a sixth lens 232 is positioned between opposing first and second mirrors 230 and 234, which is in perpendicular relation to the first, third and fourth axes 400, 404 and 406. The sixth lens 232 is positioned one focal length from the contracted fluorescence emissions 205B and the galvanometer mirror 218 and serves to Fourier-transform the contracted fluorescence emissions 205B onto the galvanometer mirror 218. In this arrangement, the galvanometer 218 and the seventh lens 238 serve to rescan the contracted fluorescence emissions 205B that forms an image onto a detector component 240, such as a camera, to capture the image.

Figure 3:
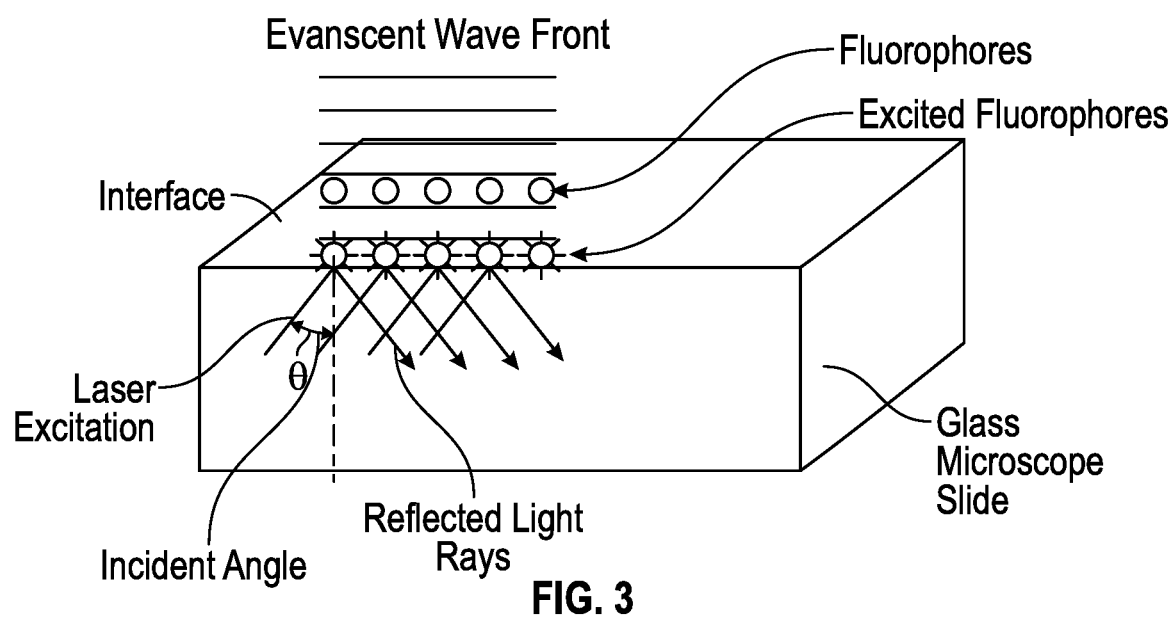
FIG. 3 is an illustration showing the reflected light rays and the effect of the evanescent wave on the instant TIRF/SIM system, according to aspects of the present disclosure.

In some embodiments of the instant TIRF/SIM system 300 the excitation micro lens array 106 may be replaced by a spatial light modulator 304 or other element that enables the phase of the excitation beam 303 to be manipulated while also generating a patterned illumination at the sample 324. By generating an appropriate pattern on the spatial light modulator 304, unwanted interference that would otherwise arise due to the interaction of the high angle, annular structured illumination can be minimized. The front face of the spatial light modulator 304 is imaged onto the sample 324 as indicated by the optical system illustrated in FIG. 4. All other optics are the same or similar to the first embodiment of the instant TIRF/SIM system 100 illustrated in FIG. 1. In one embodiment, the excitation pattern produced by the spatial light modulator 304 of FIG. 3 is required to have the same pitch as the second microlens array 128 of FIG. 1.

Figure 4:
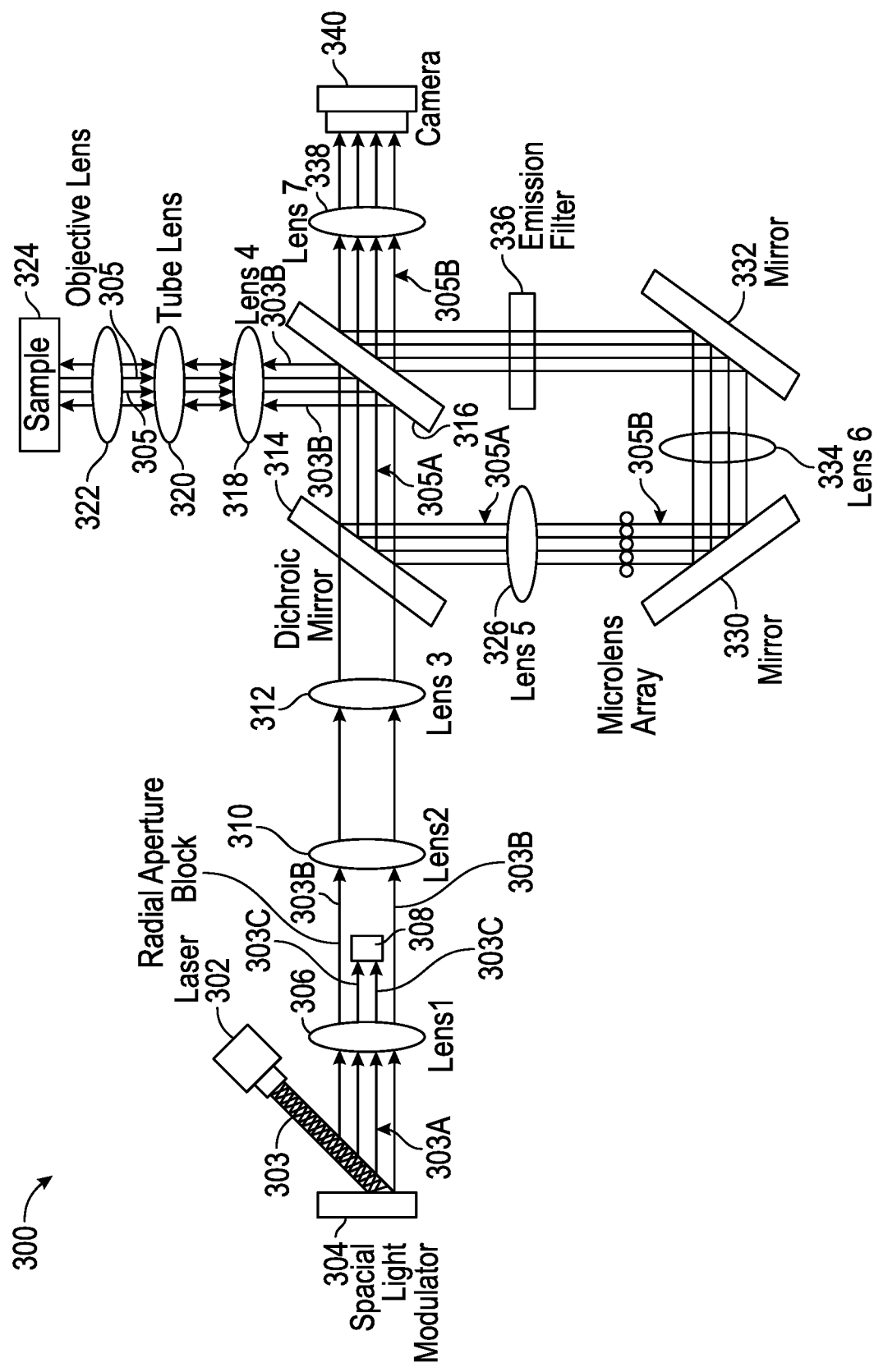
FIG. 4 is a simplified illustration showing a third embodiment of the instant TIRF/SIM system with a spatial light modulator in combination with a radial aperture block, according to aspects of the present disclosure.

Referring to FIG. 4, a third embodiment of the instant TIRF/SIM system, designated 300, implements a radial aperture block 308 positioned at a plane conjugate to the back focal plane of the objective lens 322, thus allowing only marginal, annular excitation light beams 303B to pass through for scanning onto a sample 324. Alternatively, the radial aperture block 308 may be replaced by a digital micromirror device (not shown) and enabling additional functionality (i.e., nm localization in the z direction). In this embodiment, the instant TIRF/SIM system 300 includes an excitation source 302, for example a laser component, that generates an excitation beam 303 which is transmitted onto a spatial light modulator 304 that splits the excitation beam 303 into an array of excitation foci 303A. A first lens 306 is positioned one focal length away from the focal point of the spatial light modulator 304. In addition, a radial aperture block 308 is positioned at the front focal plane of the first lens 306 to block central rays 303C emerging from the first lens 306, thereby allowing only high-angle, marginal rays 303B emerging from the first lens 306 to pass through the radial aperture block 308.

An imaging telescope arrangement includes a second lens 310 in line with a third lens 312 that collectively image the high-angle marginal rays 303B that pass through the radial aperture block 308. The second and third lenses 310 and 312 image the high-angle marginal rays 303B to pass through a dichroic mirror 314 and onto a two-sided galvanometric mirror 316. In some embodiments, the second and third lenses 310 and 312 are separated by the sum of their respective focal lengths. The galvanometric mirror 316 redirects and scans the high-angle marginal rays 303B through a fourth lens 318 in line with a tube lens 320 and onto the back focal plane of a high numerical aperture objective lens 322. This optical arrangement produces a structured illumination that does not propagate into the sample 324, but evanescently excites the sample 324 with the high-angle marginal rays 303B being imaged onto the sample 324 by the objective lens 322. Since the high-angle marginal rays 303B impinge upon the sample 324 at an angle that exceeds the critical angle, the high-angle marginal rays 303B do not propagate into the sample 324, instead causing only an evanescent wave that decays exponentially within the sample 324. The evanescent wave (caused by the high angle, marginal rays 303B that are created by the radial annular block 308) produces very sharp/high contrast excitation at the sample 324. In some embodiments, the objective lens 322 may have a numerical aperture >1.4 NA (i.e. greater than the refractive index of the sample), such as 1.65 NA or 1.70 NA.

The resulting excitation 305 generated by the sample 324 scanned by the galvanometer mirror 316 produces a patterned fluorescence emission 305A that may be collected in epi-mode, and then descanned by the galvanometric mirror 316 as the fluorescence emissions 305A are imaged by the arrangement of the objective lens 322, tube lens 320 and fourth lens 318 aligned with the galvanometric mirror 316. The fluorescence emissions 305A are then separated from the resulting excitation 305 via the dichroic mirror 314 that redirects the fluorescence emission 305A.

In some embodiments, a fifth lens 326 is positioned one focal length from the galvanometric mirror 316. The fifth lens 326 focuses the descanned fluorescence emission 305A through a micro lens array 328. In some embodiments, the micro lens array 328 has a pitch/pattern and lens spacing such that the fluorescence emissions 305A are locally contracted into contracted fluorescence emissions 305B without inversion or changing the relative distance between adjacent fluorescence emissions 305A.

When the contracted fluorescence emissions 305B are locally contracted the "contraction factor" depends on the respective wavelengths of the excitation beam 303 and fluorescence emissions 305A, the pattern displayed on the spatial light modulator 304, and the characteristics of the radial aperture block 308, and in most cases, may be set at a value of 2. In some embodiments, a sixth lens 334 is positioned between opposing first and second mirrors 330 and 332. The sixth lens 334 is positioned one focal length from the contracted fluorescence emissions 305B and the galvanometer mirror 316 and serves to Fourier-transform the contracted fluorescence emissions 305B onto the galvanometer mirror 316. In this arrangement, the galvanometer mirror 316 and the seventh lens 338 serve to rescan the contracted fluorescence emissions 305B that forms an image onto a detector component 340, such as a camera, to capture the image.

In some embodiments, an emission filter 336 may be interposed between the second mirror 332 and the galvanometer 316 to remove any residual resulting excitation 305 from the contracted fluorescence emissions 305B.

Figure 5:
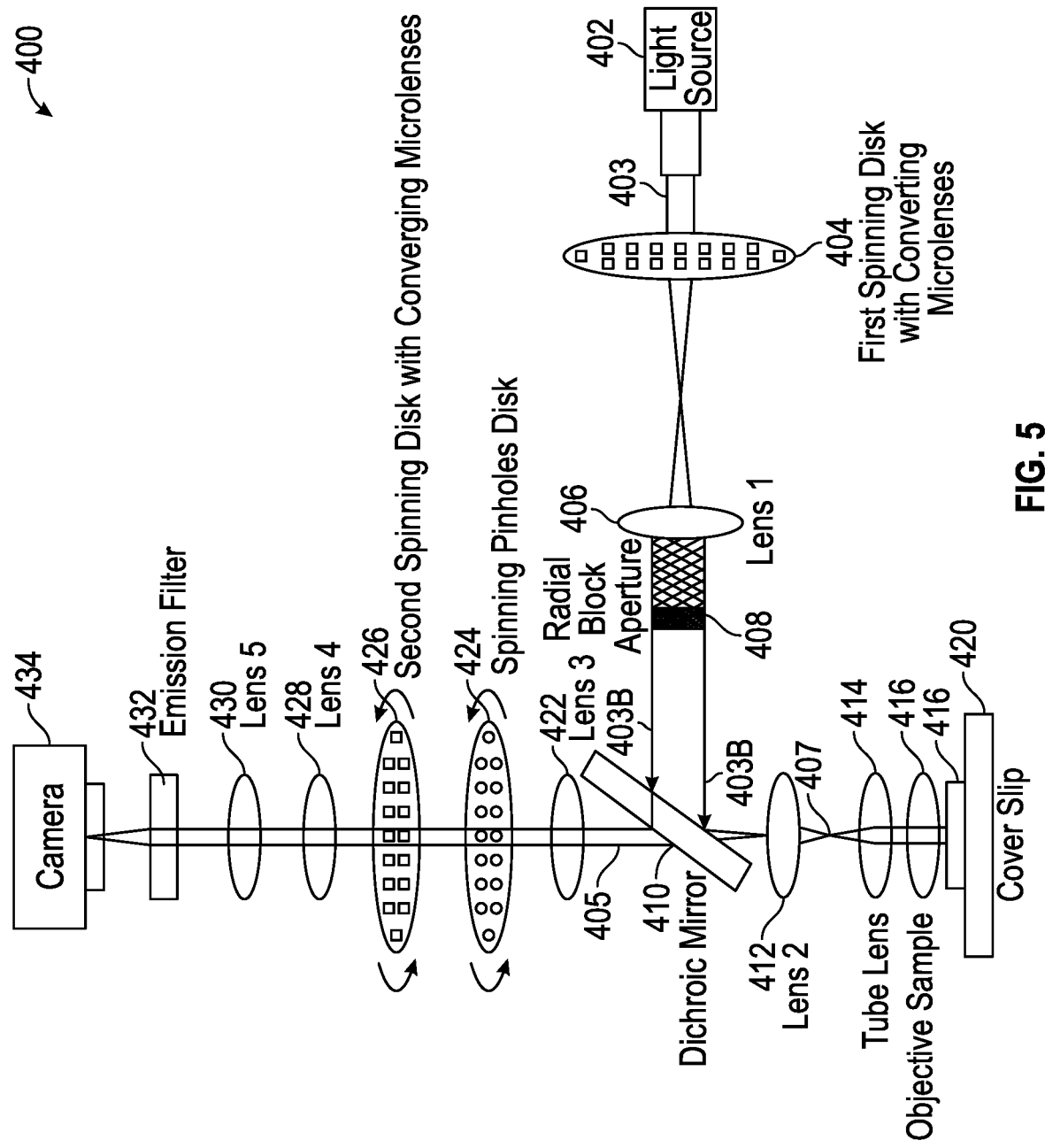
FIG. 5 is a simplified illustration showing a fourth embodiment of the instant TIRF/SIM system with a spinning disk implementation, according to aspects of the present disclosure.

Referring to FIG. 5, a fourth embodiment of the instant TIRF/SIM system, designated 400, implements a spinning disk arrangement of the instant TIRF/SIM system 400. In this embodiment, the instant TIRF/SIM system 400 includes an excitation source 402, for example a laser component, that generates an excitation beam 403 which is transmitted through a first spinning disk 404 of converging microlenses that produces a plurality of excitation foci 403A in which the excitation foci 403A cover the entire imaging field of a sample 418. As shown, in some embodiments a first lens 406 forms a telescopic arrangement with second lens 412 that relays the plurality of excitation foci to an intermediate image plane 407 after reflecting off a dichroic mirror 410 that is positioned between the first lens 406, which is located one focal length away from the plurality of excitation foci 403A, and the second lens 412. In addition, a radial aperture block 408 is positioned at the co-focal point between the first lens 406 and the second lens 412 in order to filter low angle excitation foci 403A that would otherwise produce subcritical, propagating excitation foci into the sample 418. As noted above, the radial aperture block 408 blocks central rays of the excitation foci 403A emerging from the first lens 406, thereby allowing only high-angle, marginal rays 403B emerging from the first lens 406 to pass through the radial aperture block 408.

As further shown, the high-angle, marginal rays 403B are relayed from the intermediate image plane 407 to the sample 418 via the telescope formed by the arrangement of a tube lens 414 and the objective lens 416. The objective lens 416 may have a higher NA than the refractive index of the sample 418, e.g., numerical aperture greater than 1.33, to ensure TIRF conditions are produced. In some embodiments, the focal lengths and placement of the second lens 412 and the tube lens 414 may be chosen so that the radial aperture block 408 is imaged to the back focal plane of the objective lens 416. Once the sample 418 is illuminated by the high-angle, marginal rays 403B, the fluorescent emissions 405 emitted by the sample 418 is collected in epi-mode and relayed through the second lens 412 and then a third lens 422 (after passing through the dichroic mirror 410) to a spinning pinhole disk 424 having the same pitch/spacing as the first spinning disk 404 with converging microlenses. The spinning pinhole disk 424 serves to reject scattered fluorescent emissions 405 and unwanted sidelobes in the fluorescent emissions 405. After the fluorescent emissions 405 pass through the spinning pinhole disk 424, a second spinning disk 426 with converging microlenses having the same pitch/spacing as the spinning pinhole disk 424 and first spinning disk 404 is used to locally contract each fluorescent foci of the fluorescent emissions 405 with a contraction factor of approximately 2 using the scaling operation illustrated in FIGS. 18 and 19, thereby producing contracted, non-inverted fluorescent foci 405A. The respective focal lengths of the first and second spinning disks 404 and 426 and the placement of the second spinning disk 426 are chosen to locally contract the fluorescent foci of the fluorescent emissions 405 the desired degree without inverting the fluorescent foci with respect to the overall image of the sample 418. Finally, the contracted, non-inverted fluorescent foci 405A are relayed to an imaging camera 434 via a final telescope arrangement of a fourth lens 428 and fifth lens 430. In some embodiments, an emission filter 432 may be positioned in the emission path to reject excitation light. In some embodiment, the first and second spinning disks 404 and 426 and the spinning pinhole disk 424 may be spun in tandem to produce a super-resolution image during a single camera exposure. In some embodiments, the sample 418 may be disposed on a coverslip 420 when illuminated by a high angle, marginal rays 403B.

Test Results

Figure 6:
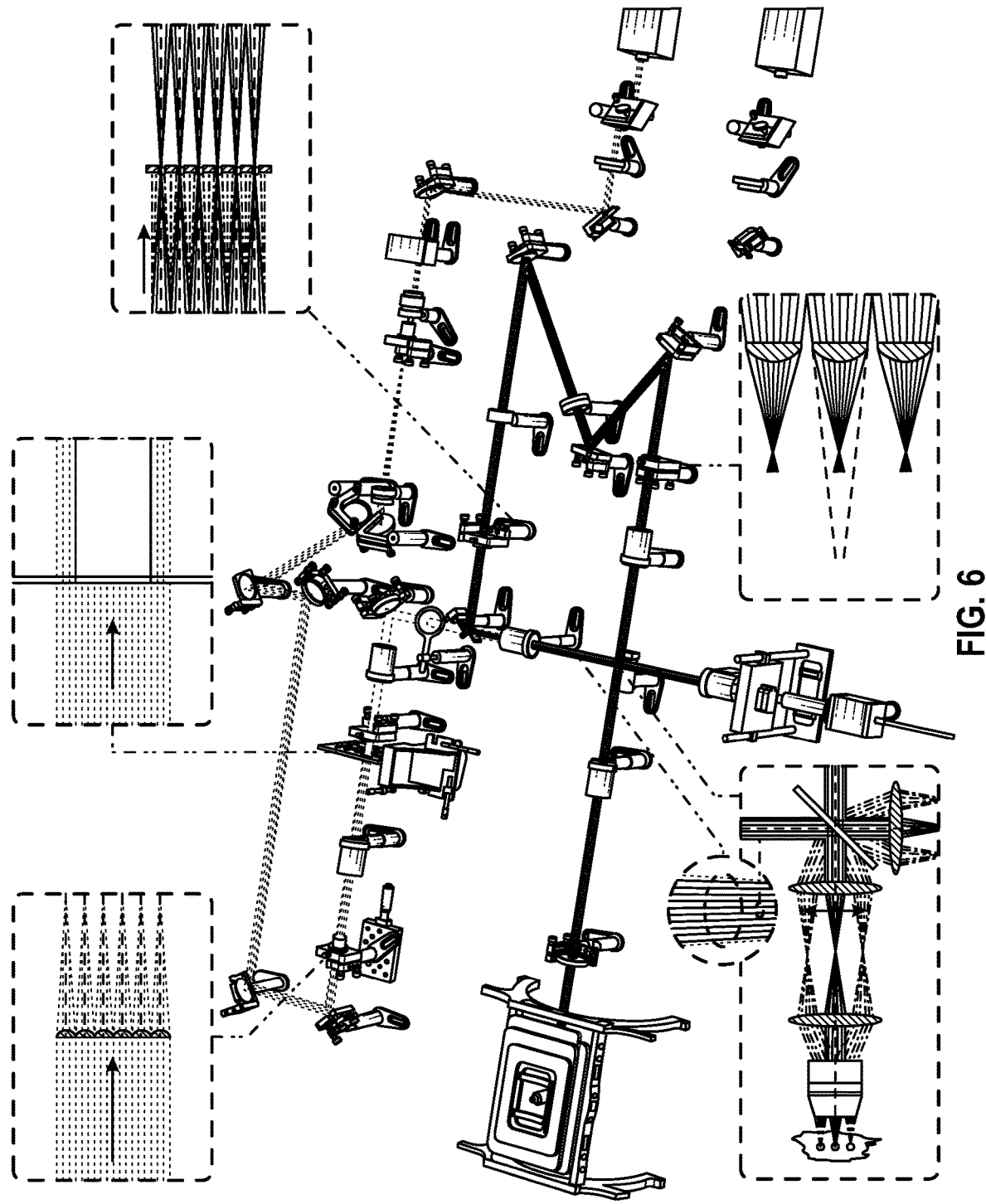
FIG. 6 is an illustration showing a working model of the first embodiment of the instant TIRF/SIM system, according to aspects of the present disclosure.

Referring to FIG. 6, a working model used for testing of the instant TIRF/SIM system 100 is illustrated. In some embodiments, the instant TIRF/SIM system 100 includes a pair of 488 nm and a 561 nm lasers which are combined and passed through an acousto tunable filter (AOTF) for shuttering, expanding the beam and spatially filtering (e.g., f–45 mm and f=400 mm achromats with 100 μm pinhole placed at the co-focal point between the lenses) and directed to an excitation microlens array. In addition, an opaque circular mask was positioned at the co-focal point between scan lens 1 and scan lens 2 (e.g., one focal length from the excitation foci produced by the microlens array) that collectively functioned to block subcritical excitation rays, thereby producing annular illumination of the sample. For clarity, only on-axis excitation foci produced by the central microlenses are illustrated after the mask. As shown, scan lens 2 and scan lens 3 relay the mask to a two-sided galvanometric mirror after passing through a compensator plate for reducing astigmatism that would otherwise result as the excitation foci is transmitted through a thick dichroic mirror. A tube lens in combination with scan lens 4 was used to further magnify and relay the mask to the back focal plane of a high NA objective (e.g., NA=1.7). The scanning of the galvanometric mirror translates the TIRF excitation pattern at the sample. Once the sample was scanned and illuminated, fluorescence emissions from the sample were collected along the same optical path, descanned from the galvanometric mirror and reflected off of the dichroic mirror. Emission-side optics are nearly identical to those used in the description of the instant TIRF/SIM system 100. Note that the distances and ray diagrams shown in FIG. 6 are approximate renderings.

As noted above, TIRF is enabled when highly inclined light with incidence angle $\Theta \geq \Theta_c = \arcsin(n_2/n_1)$ impinges upon the boundary between media with indices $n_1$ and $n_2$, with $n_1 > n_2$. The inventors reasoned that placing an annular mask at a Fourier image plane (optically conjugate to the back focal plane of the objective) would block all subcritical rays, thereby enforcing TIRF without otherwise perturbing the speed and functionality of the original instant SIM system. Annular illumination has been used to produce a single TIRF spot in diffraction-limited and stimulated emission depletion microscopy, yet for parallelized instant SIM an array of spots is needed.

The inventors created such a pattern by placing an annulus one focal length away from the foci produced by our excitation microlens array, thus filtering out low angle rays in each excitation focus simultaneously. The resulting beams were relayed to the sample by previous instant SIM optical components, including a two-sided galvanometric mirror conjugate to the back focal plane of the objective (a 1.7 numerical aperture (NA) lens used for the large range of accessible $\Theta \geq \Theta_C$, facilitating TIRF). Emission optics were near identical to the original instant SIM setup (Methods), and included pinhole- and emission microlens arrays with appropriate relay optics as shown in FIG. 6.

Figures 11A, 11B, 11C:
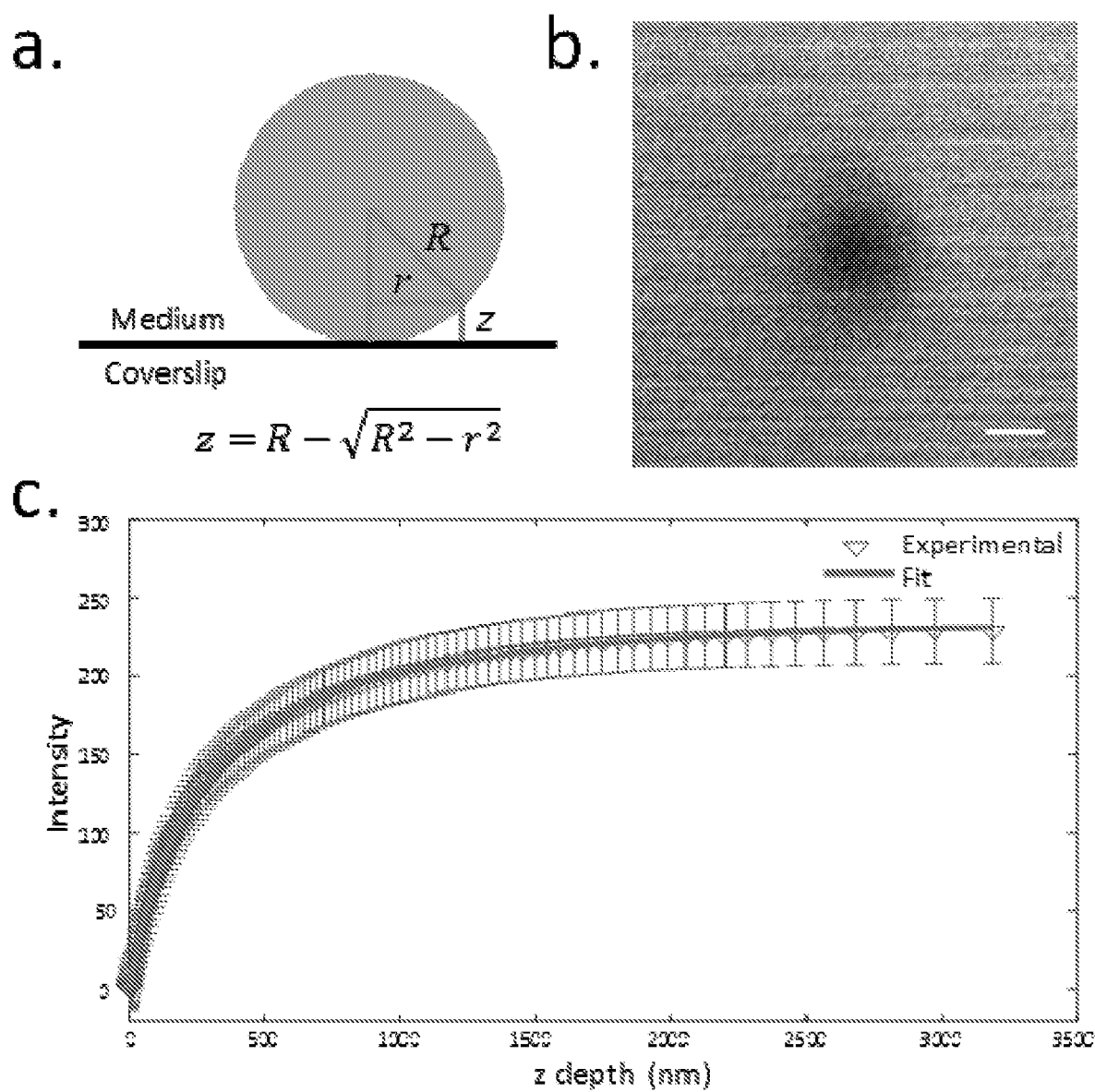
FIGS. 11A-11C show an estimation of evanescent field decay length with silica beads placed in a fluorescent dye, according to aspects of the present disclosure.
Figures 12A, 12B, 12C, 12D:
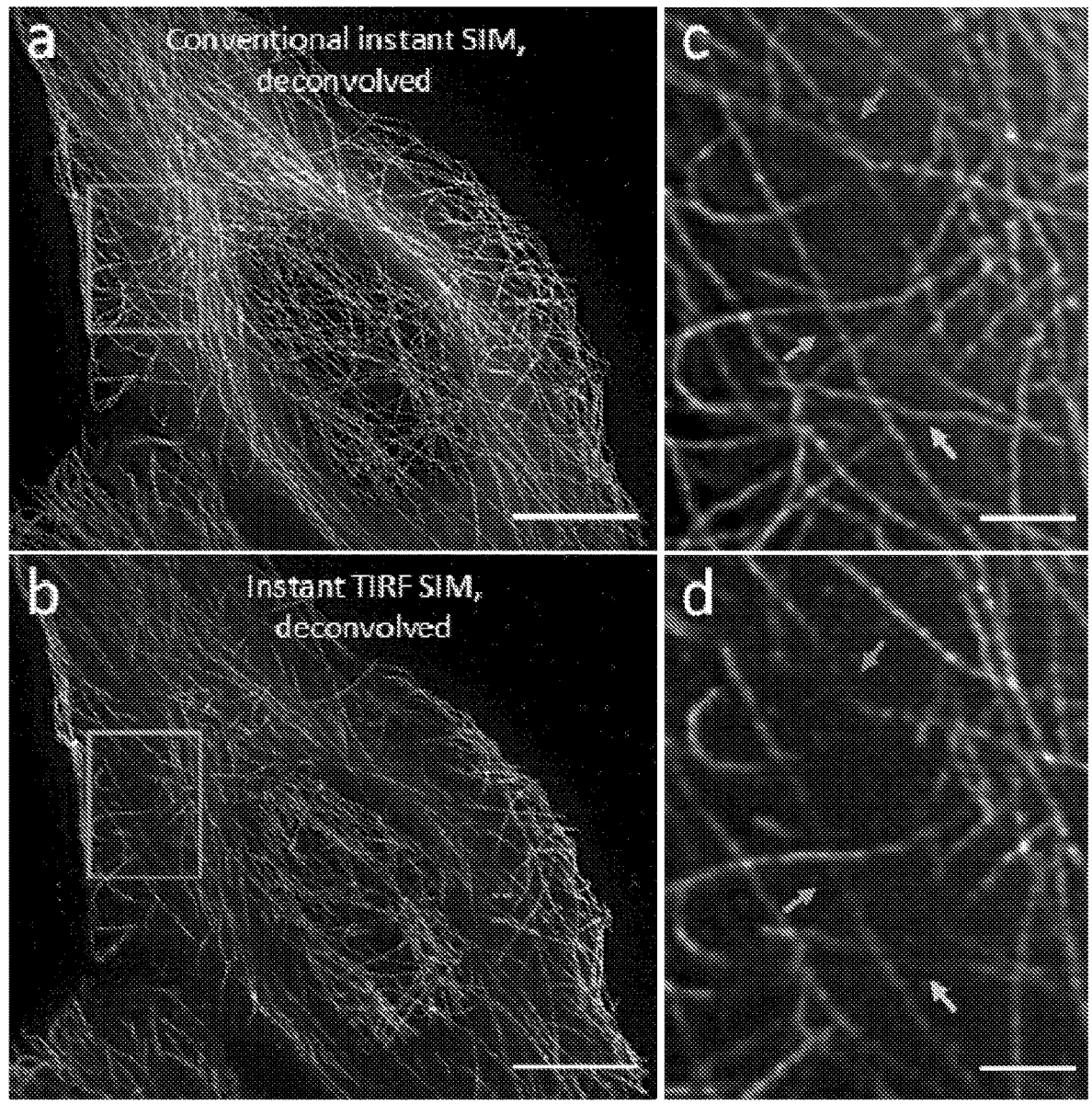
FIGS. 12A-12D show comparative images between a conventional instant SIM system and the instant TIRF/SIM system, according to aspects of the present disclosure.
Figures 13A, 13B, 13C, 13D, 13E, 13F:
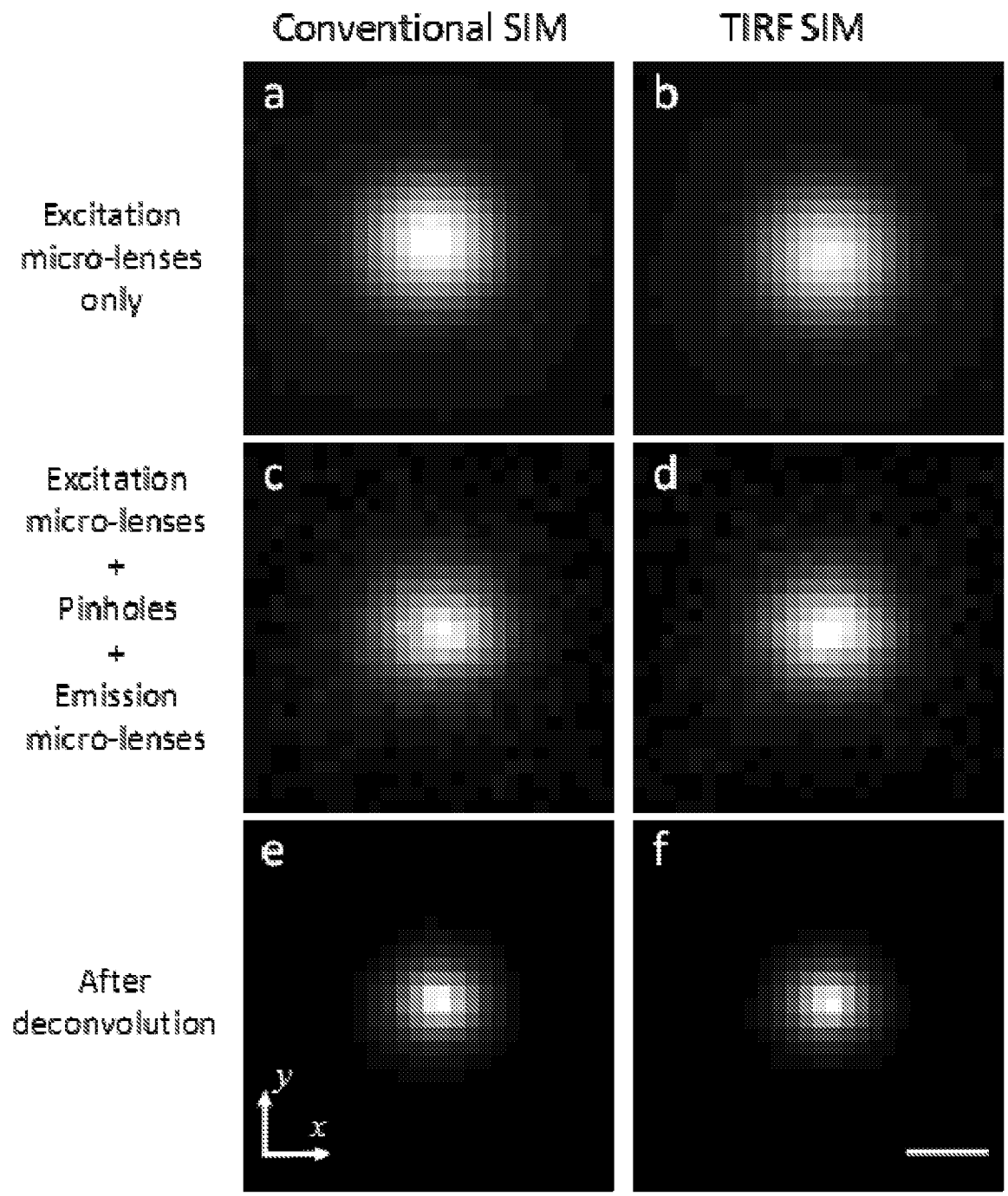
FIGS. 13A-13F show comparative representative bead images between a conventional SIM system and the instant TIRF/SIM system, according to aspects of the present disclosure.
Figures 14A, 14B:
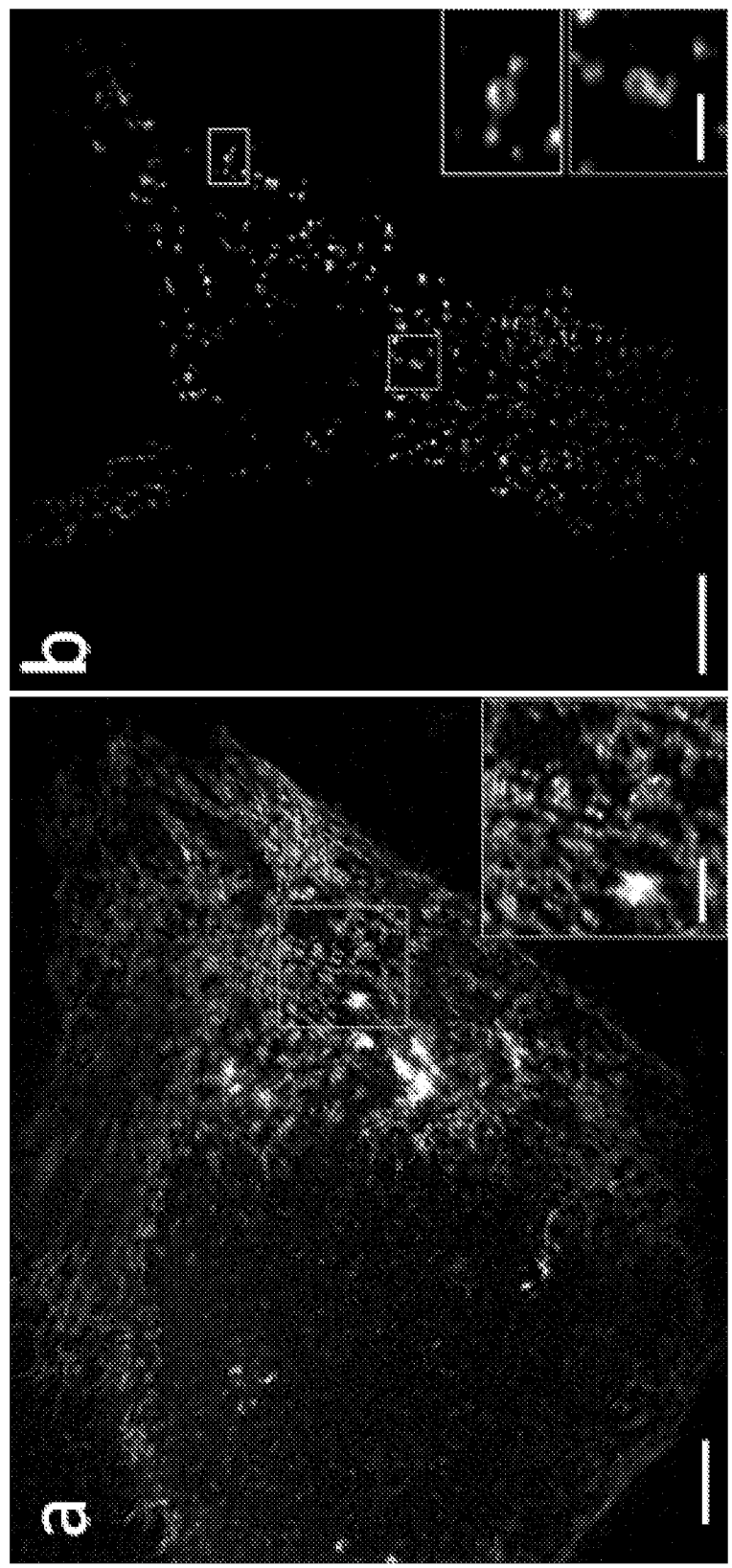
FIGS. 14A and 14B show biological resolution standards for the instant TIRF/SIM system, according to aspects of the present disclosure.

Since annular excitation produces a focused spot with pronounced sidelobes (due to the Bessel-like character of the excitation), the inventors were concerned that interference between neighboring foci and transfer of energy from the central intensity maxima to sidelobes would significantly diminish illumination contrast in the focal plane. Indeed, when imaging fluorescent dye in TIRF mode, substantial background fluorescence was observed between excitation foci (albeit still less than observed when imaging conventionally, due to the dramatic reduction of out-of-focus fluorescence in TIRF). However, individual foci were sharply defined and the extraneous background could be readily removed with the pinhole array intrinsic to the setup as shown in FIGS. 10A-10I. The tests confirmed that TIRF was maintained during the imaging process by measuring the depth of the evanescent field with index-matched silica beads as shown in FIGS. 11A-11C, which found this value to be 123 nm (117 nm, 129 nm, 95% confidence interval). Qualitative comparisons on fixed microtubule samples also demonstrated the improved sectioning in TIRF relative to conventional instant SIM are shown in the images of FIGS. 12A-12D.

Figures 7A, 7B, 7C, 7D, 7E:
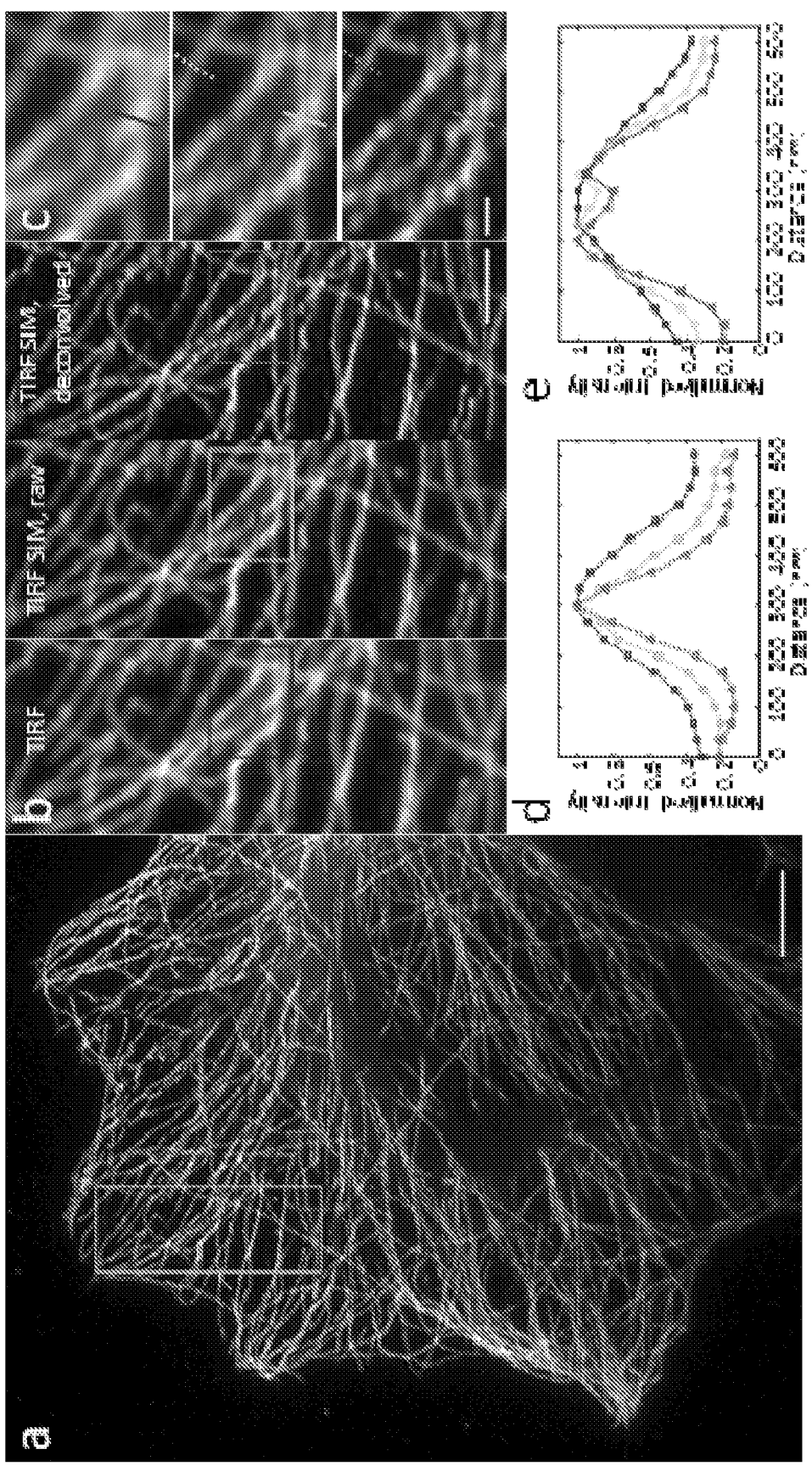
FIGS. 7A-7C show various images taken with the instant TIRF/SIM system and FIGS. 7D and 7E are graphical representations showing comparative line profiles, according to aspects of the present disclosure.

The test system measured system resolution on 100 nm fluorescent beads shown in FIGS. 13A-13F. With scanned TIRF excitation only, the fluorescent beads were resolved to 249+/−11 nm (N=20 beads). Performing operations, such as descanning, pinholing, locally contracting, and rescanning reduced the apparent fluorescent bead diameter to 194+/−20 nm, and resolution could be further improved after deconvolution (10 iterations, Richardson-Lucy deconvolution) to 115+/−13 nm. These results were similar to those obtained using conventional illumination with the same objective lens, i.e. with conventional instant SIM implying that the spatial resolution did not degrade in TIRF. Images of fixed cells further confirmed this progressive resolution improvement as shown in FIGS. 7A-7E, as individual microtubules had an apparent width of ~128 nm (FIG. 7D) and the inventors were able to distinguish microtubules spaced 134 nm apart (FIG. 7E). Qualitative tests in living cells confirmed this resolving power (FIGS. 14A and 14B), as individual GFP-labeled myosin IIA heads and void areas within GFP-FCHO2 puncta, subdiffractive structural features that have previously been resolved with TIRF/SIM were discerned.

Figures 8A, 8B, 8C, 8D, 8E, 8F, 8G, 8H:
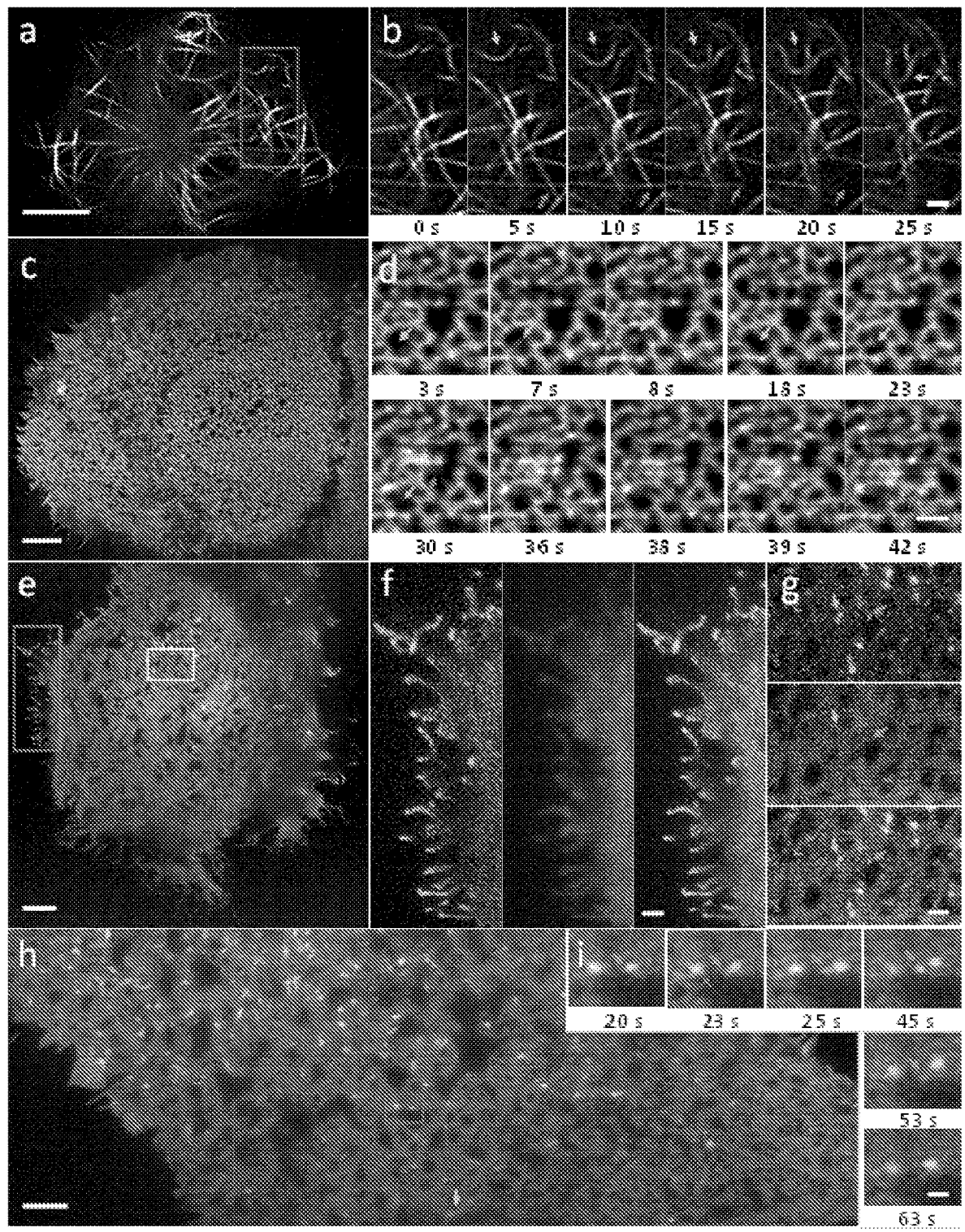
FIGS. 8A-8H show various images taken with the instant TIRF/SIM system of protein distributions in the vicinity of the plasma membrane over hundreds of time points, according to aspects of the present disclosure.
Figures 15A, 15B:
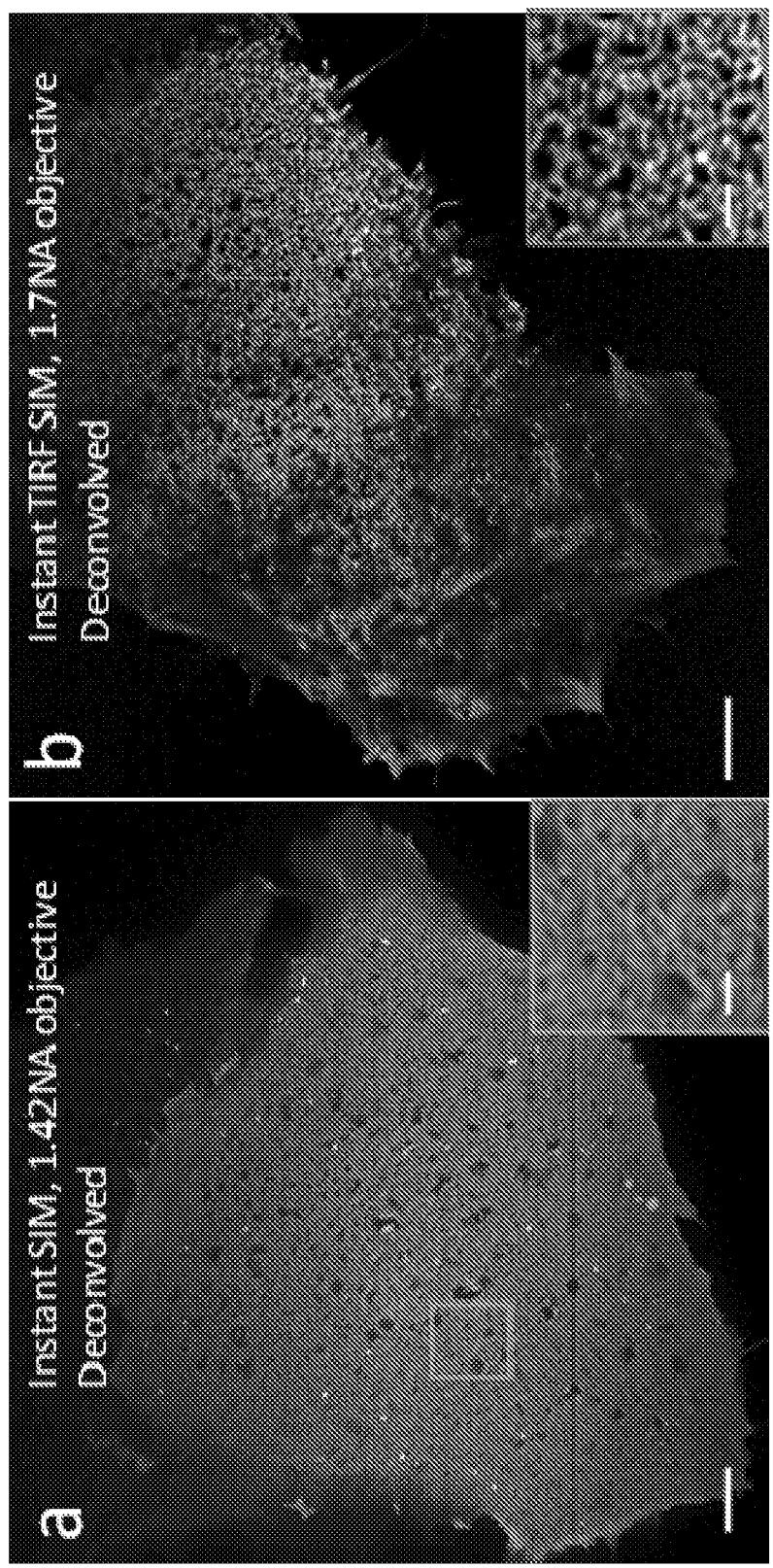
FIGS. 15A and 15B show comparative images of a conventional SIM system and the instant TIRF/SIM system, according to aspects of the present disclosure.
Figures 16A, 16B, 16C, 16D:
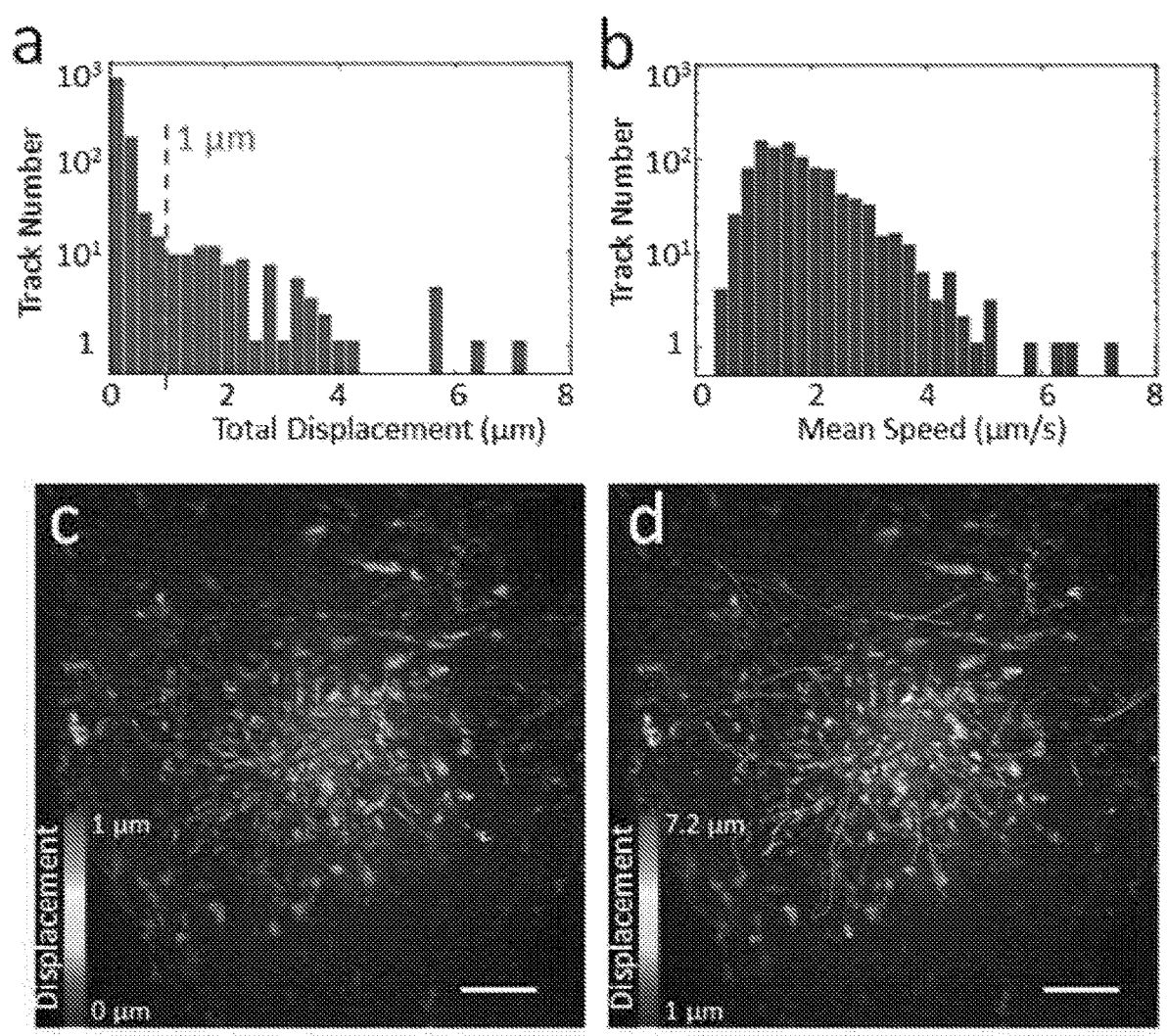
FIGS. 16A-16D are histograms of total displacement and mean speed of tracked particles, according to aspects of the present disclosure.

The test used the instant TIRF/SIM system 100 to examine the dynamics of protein distributions in living cells (FIGS. 8A-8H). First, the test recorded microtubule dynamics over 500 time-points by imaging 3×-EGFP-EMTB in Jurkat T cells after they settled on anti-CD3 antibody coated coverslips (FIG. 8A). The imaging rate of 20 Hz was sufficient to easily follow buckling, shortening, and sliding of microtubule bundles at the base of the cell within the evanescent TIRF field (FIG. 8A). As a second example, the test recorded the dynamics of the small GTPase HRas, which is lipidated and then targeted to the plasma membrane 15. Images were acquired every 0.75 s over 100 timepoints in U2OS cells (FIG. 8C). Intriguingly, GFP-HRas localized in highly active microdomains at the plasma membrane (FIGS. 8C and 8D). The high spatiotemporal resolution of the technique revealed rich dynamics of this reticulated pattern, as the test observed reorganization of domains on the second timescale, including transient 'filling in' of the void areas between microdomains (FIG. 8D), and coordinated, 'wave-like' motion between microdomains. Neither the distribution nor the dynamics of Ras have been previously reported at this length scale in living cells, perhaps due to the lack of spatial resolution or optical sectioning (e.g. in conventional instant SIM at lower NA, microdomains were poorly resolved (FIGS. 15A and 15B).

The test also imaged Halotag-HRAS (labeled with Janelia Fluor 54916) in combination with GFP-VSVG (FIG. 8E), highlighting the ability of instant TIRF SIM for live, dual-color imaging at the plasma membrane. VSVG showed some localization around Ras microdomains within the cell interior (FIG. 8G), but the inventors also observed preferential enrichment of VSVG at the cell boundary, particularly at cell filopodia and filamentous structures. In a second dual-color example, GFP-HRAS was imaged with dsRED-ER (FIG. 8H), marking the endoplamic reticulum (ER). Given the optical sectioning of the technique, the ER mostly appeared as a set of punctate spots and occasional tubules, presumably representing ER proximal to the plasma membrane. Although punctate ER structures occasionally colocalized with Ras, the protein distributions were mostly distinct and exhibited different dynamics consistent with their differential localization and function within the cell. The spatial resolution of the technique proved helpful in resolving the fission of Ras microclusters adjacent to more stable ER contacts, a phenomenon otherwise obscured by diffraction (FIG. 8I).

The test allowed visualization of intracellular calcium flux, actin, and myosin IIB dynamics in live cells. These examples all underscore the ability of instant TIRF SIM to enable super-resolution imaging well matched to the dynamics of interest, either matching or surpassing the image acquisition rate offered by more classic TIRF SIM systems.

Figures 9A, 9B, 9C, 9D, 9E, 9F:
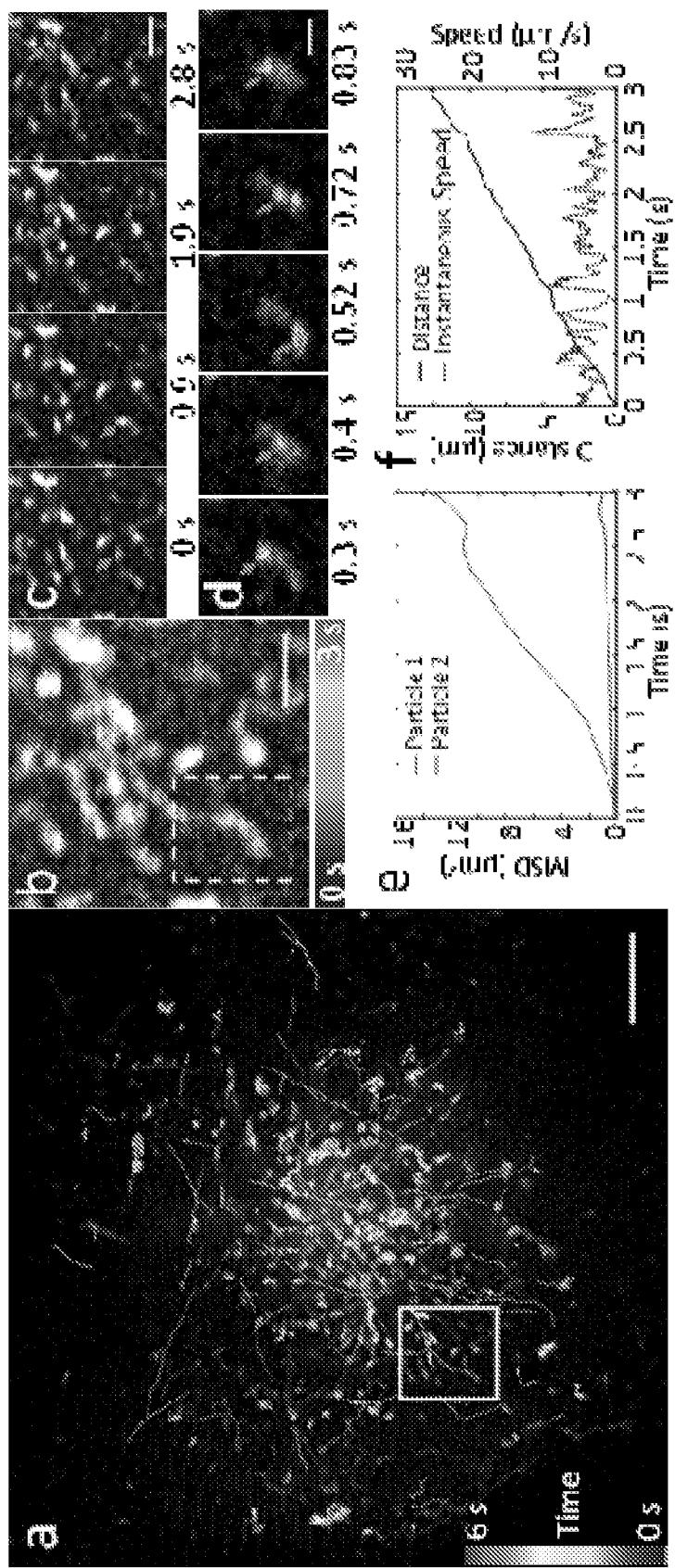
FIGS. 9A-9F show various images taken with the instant TIRF/SIM system of Rab11 transfected into U2OS cells, according to aspects of the present disclosure.
Figures 10A, 10B, 10C, 10D, 10E, 10F, 10G, 10H, 10I:
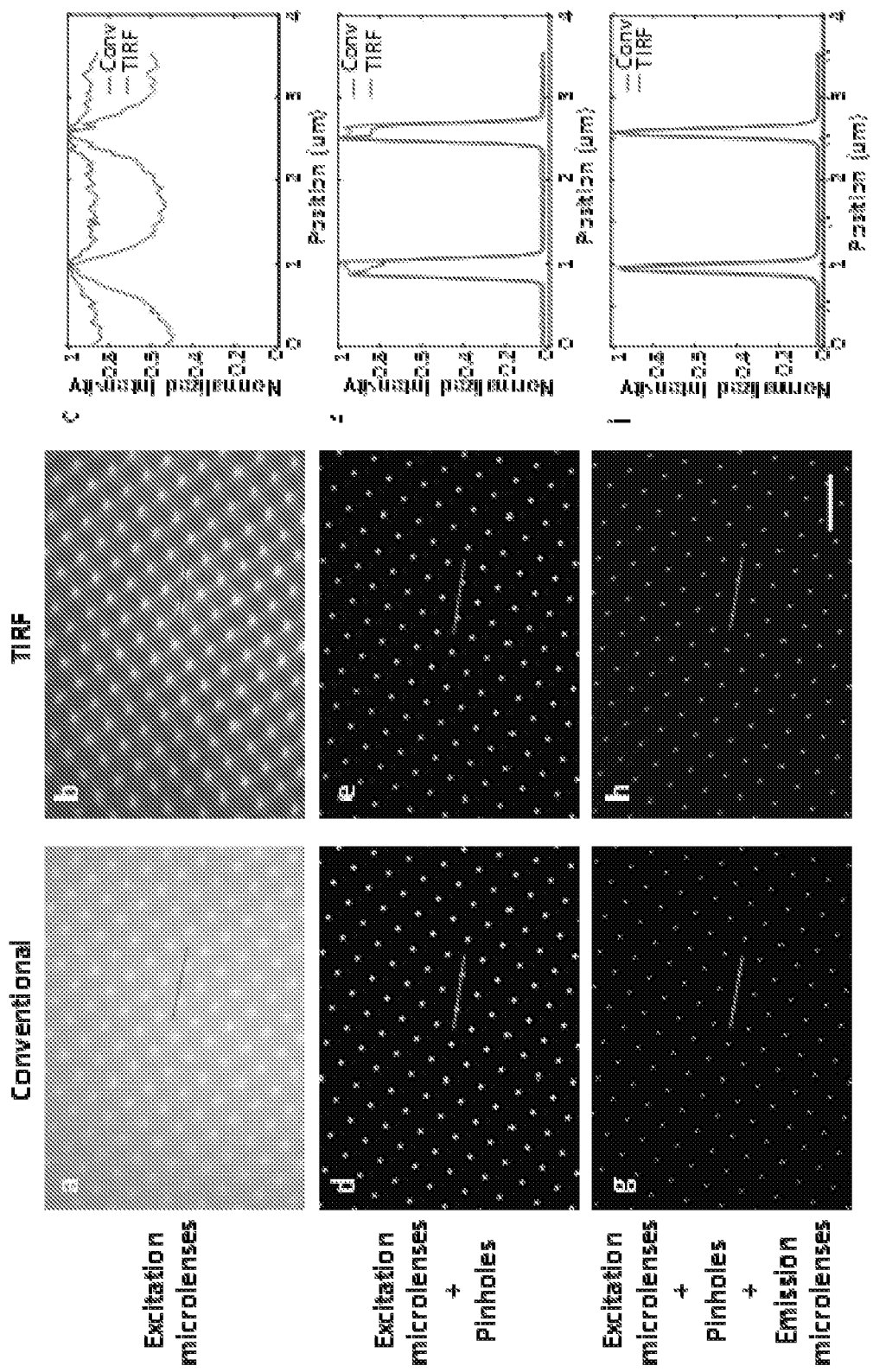
FIGS. 10A-10I show a comparison of excitation and emission patterns between conventional microscopy and the instant TIRF/SIM system, according to aspects of the present disclosure.
Figures 17A, 17B:
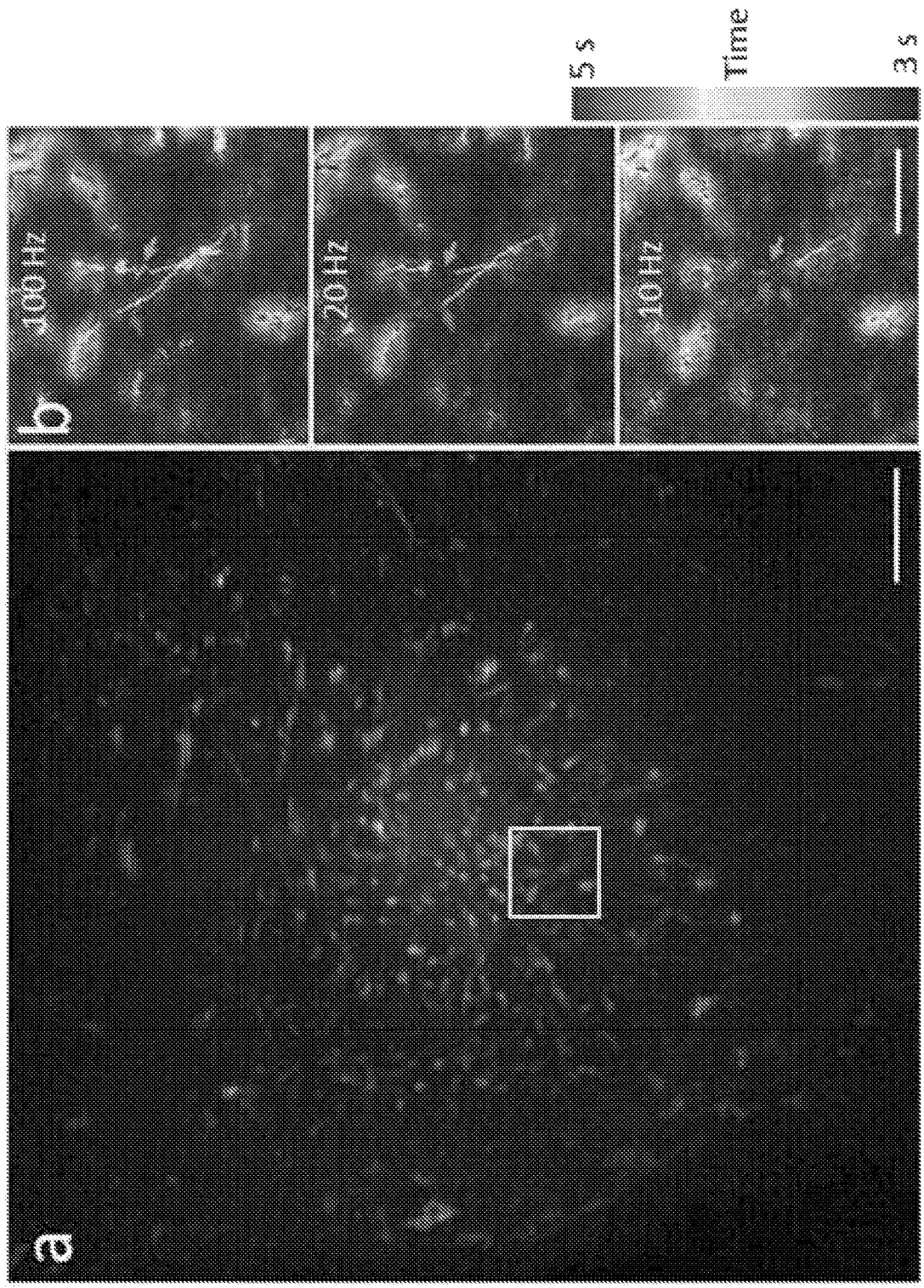
FIGS. 17A and 17B show images illustrating the effect of temporal undersampling on automated tracking, according to aspects of the present disclosure.

A key advantage, however, in instant SIM is the ability to image at much faster frame rates since the super-resolution image is formed in a single camera exposure. To illustrate this capability, the test imaged GFP-Rab11 in U2OS cells at 37° C. at 100 Hz. This imaging rate was sufficient to visualize and track the rapid motion of 980 Rab11 decorated particles (FIG. 9A). An analysis of track motion revealed that the majority of particles underwent <1 μm displacement over our 6 seconds imaging period; yet, tens of particles were observed that showed greater displacements (FIGS. 16A-16D). It was observed that particles that traveled further also traveled faster, with mean speed greater than 1 μm/s (FIGS. 16A-16D) and instantaneous speed in some cases exceeding 10 μm/s (FIGS. 9D and 9F). A closer analysis at the single particle level shown in FIGS. 9B and 9C also revealed qualitative differences in particle motion, with some particles undergoing diffusive motion, as revealed by a linear mean square displacement (MSD) vs. time and others showing supralinear MSD vs. time (FIG. 9E) with bouts of directed motion illustrated in FIG. 9D. It was noted that imaging at slower frame rates would artificially shorten track lengths, offering a less accurate representation of the underlying motion (FIGS. 17A and 17B).

The Instant TIRF-SIM system 100 provides fundamentally faster operation than classic TIRF-SIM systems, as only one image needs to be acquired, instead of the standard nine. Additional advantages of the implementation over alternative approaches include less read noise (since fewer images are acquired) and less computational processing (the method requires only simple deconvolution of the raw images, instead of extensive image processing in Fourier space). Although the spatial resolution we report (~115 nm) is ~40% less than claimed in previous state of the art linear TIRF-SIM, the existing implementation of instant TIRF-SIM is ~50 fold faster, as the test shown in FIG. 9 demonstrated by imaging at frame rates up to 100 Hz Methods—Instant TIRF-SIM The instant TIRF SIM 100 used a 1.7 NA objective (Olympus, APON100XHOTIRF) for excitation and detection. When imaging into aqueous samples with refractive index 1.33, $1-(1.33/1.7)=0.22$ of the objective back focal plane diameter ($d_{BFP}$) is available for TIRF, implying that sub-critical illumination rays within a diameter $0.78*d_{BFP}=0.78*2*NA_{OBJ}*=0.78*2*1.7*1.8$ mm=4.77 mm must be blocked. Second, a relay system was inserted into the excitation arm of the instant SIM to block these rays. Excitation from 488 nm and 561 nm lasers was combined and beam expanded as before, and directed to a microlens array (Amus, f=6 mm, 222 mm spacing between microlenses, 1 mm thick, 25 mm diameter, antireflection coated over 400-650 nm, APO-Q-P222-F6(633)+CHR) to produce an array of excitation foci. The test used a matched pair of scan lenses (Scan lens 1 and 2, f=190 mm, Special Optics, 55-S190-60-VIS) placed in 4f configuration to relay these excitation foci to the rest of the optical system, inserting an opaque circular mask (Photosciences, 2.68 mm diameter chrome circle with optical density 5 on 4"×4"×0.090" quartz wafer) at the focal point between scan lenses (and the Fourier plane of the excitation foci produced by the microlens array) to filter subcritical rays. Given the 350 mm/190 mm=1.84× magnification between mask and the back focal plane of the objective, the mask was designed to block the central 2.68 mm*1.84=4.93 mm diameter of the illumination. An iris placed just after the mask ensured that the outer diameter of the beam was ~3.33 mm, a diameter that magnified to 3.33*1.84=6.13 mm, or $\sim d_{BFP}$, thereby reducing stray light that would otherwise fall outside the objective back focal plane. Alignment of the opaque mask and microlens array were greatly aided by placing the former on a 3-axis translation stage (Thorlabs, LT3, used for correct positioning of the mask image at the back focal plane) and the latter on a uniaxial translation stage (Thorlabs, LNR50M, used to position excitation foci precisely at the focal plane of the objective lens). An alignment reticle (Leica) that screwed into the objective turret was used to further check that the annular illumination pattern was properly positioned (concentric with the optical axis of the objective) and focused at the back focal plane of our objective.

In the emission path, optics were identical to the previous instant SIM design, except that a pinhole array with larger pinholes (Photosciences, Chrome on 0.090" thick quartz, 222 μm pinhole spacing, 50 μm pinhole diameter) and an emission side microlens array with longer focal length (f=1.86 mm, Amus, APO-Q-P222-F1.86(633)) were used. The total magnification between sample and our scientific grade complementary metal-oxide semiconductor camera (PCO-TECH, pco.edge 4.2) detector was 350 mm/1.8 mm=194.4, resulting in an image pixel size of 33.4 nm. These elements are shown in FIG. 6.

The excitation laser power was measured immediately prior to the objective. Depending on the sample, the average power ranged from 0.2-2 mW, implying an intensity range from ~7-70 W/cm$^2$ (given the 58 μm×52 μm field of view).

Samples were deposited on 20 mm diameter high index coverslips (Olympus, 9-U992) designed for use with the 1.7 NA lens. Coverslips were mounted in a magnetic chamber (Live Cell Instrument, CM-B20-1) that attached to the microscope stage. For temperature maintenance at 37° C., the magnetic chamber was mounted within an incubation chamber (Okolab, H301-MINI).

Estimating the Evanescent Field Depth

The inventors used two methods to estimate evanescent field depth. First, an analytical method was used. For excitation of wavelength $\lambda$ impinging at angle $\Theta_1$ upon an interface with indices $n_1$ and $n_2$, $n_1 > n_2$, the intensity I of an evanescent field decays along the optic axis with decay constant d according to $I(z) = I_0 \exp(-z/d)$, with $d = \lambda/(4\pi) (n_1^2 \sin^2(\Theta_1) - n_2^2)^{-0.5}$. The term $n_1^2 \sin^2(\Theta_1)$ is equivalent to the square of an 'effective' NA, in our case 1.7. If considering the smallest angles in the annular excitation (corresponding to the inner radius used in the mask, and producing evanescent waves with the longest decay length), this effective NA is $4.93/6.12 * NA_{OBJ} = 1.37$. Assuming $n_2 = 1.33$ and $\lambda = 488$ nm leads to d=118 nm. If considering the largest angles (corresponding to the outer annulus radius, producing evanescent waves with the shortest decay length), the effective NA is $NA_{OBJ} = 1.7$, leading to d=37 nm. By these simple calculations, the 'average' decay thus lies between 37 nm-118 nm, and is weighted by the distribution of intensity in the annular excitation.

Since such an intensity distribution is difficult to measure accurately, the inventors instead opted to more directly measure the average evanescent decay length using silica beads (diameter 7.27 µm, refractive index, 1.42, Bangs Laboratories) placed in a solution of fluorescein dye (Fluke, Cat #32615) (FIG. 11A). In this method, the known diameter of the bead is used to convert the apparent radii observed with TIRF to an axial depth, z (FIG. 11B). Following previous work, the inventors integrated the intensity I(z) from the coverslip surface to some depth z, as this corresponds to the observed signal F(z) at each depth. First, the inventors assumed the fluorescence is well modeled by a sum of two exponentials. The first term corresponds to signal derived from 'pure' TIRF (with decay d) and the second term models scattering that is known to contaminate objective-type TIRF (with decay D):

$$I(z) = A \exp(-z/d) + B \exp(-z/D),$$

where A and B are constants that account for incident beam intensity, concentration, and the relative weight of the scattering term. Integrating this expression yields $$F(z) = Ad(1 - \exp(-z/d)) + BD(1 - \exp(-z/D)).$$

Fitting the measured fluorescence intensity at each depth (derived at each bead radius) to this expression (FIG. 11C) with the Matlab curve fitting toolbox gave d=123 nm with 95% confidence interval (117 nm, 129 nm). The scattering amplitude B represented ~24% of the signal.

Data Processing

Deconvolution

Unless otherwise indicated, data presented in this test were deconvolved to further enhance spatial resolution. Before deconvolution, background was subtracted from the raw images. Background was estimated by averaging 100 'dark' images acquired without illumination. For deconvolution, the inventors used the Richardson-Lucy algorithm, blurring with a 2D PSF:

for $i = 1, 2, \ldots N$ $$\text{Estimate}_{New} = \text{Estimate}_{Previous} \times \text{Blur}\left(\frac{\text{Image}_{Measured}}{\text{Blur}(\text{Estimate}_{Previous})}\right)$$

The PSF was experimentally derived by registering and then averaging the images of 20 100 nm yellow-green beads. Deconvolution was implemented in MATLAB 2017a with the number of iterations N set to 10.

Tracking

For tracking the particles in the Rab11 dataset (FIGS. 9A-9F), the inventors performed semi-automated tracking using the TrackMate ImageJ Plugin (https://imagej.net/TrackMate). For particle detection, the Difference of Gaussian (DoG) detector was used with estimated blob diameter of 0.3 µm, and an initial quality threshold of 120. The particles were further filtered and linked with a simple Linear Assignment Problem (LAP) linker. Linking maximum distance and Gap-closing maximum distance were set to 0.3 µm, and the maximum frame gap was set to 5. For tracking on the whole image (FIGS. 9A-9F), the linking filters were manually adjusted to filter out obviously spurious tracks. Then manual editing was performed within the plugin interface to improve tracking results. For the cropped region used for downsampling analysis (FIGS. 17A and 17B), images were down-sampled 5 times and 10 times in the time domain. Then automated tracking was performed independently for the cropped images (100 Hz) and the downsampled images (20 Hz and 10 Hz) without manually adjusting either linking filters or links.

From the particle tracks (i.e., the sequences of coordinates denoting the position of each tracked particle at each time point), the inventors computed several quantitative metrics including displacement, distance, instantaneous speed, mean speed and mean squared displacement (MSD).

Given a trajectory consisting of N time points and the particle coordinates at ith time point $p_i = (x_i, y_i)$, the distance between any two points $p_i$ and $p_j$ is defined as the Euclidean norm:

$$d(p_i, p_j) = \|p_i - p_j\|$$

The total distance traversed at the jth time point is calculated from the starting point (the 1st time point) and defined as:

$$D_j = \sum_{i=1}^{j-1} d(p_i, p_{i+1})$$

and the displacement (magnitude), also known as net distance $$F_j = d(p_1, p_j)$$

Then the total distance for the whole trajectory is $D_N$ and the total displacement for the whole trajectory is $F_N$.

The instantaneous speed is defined as:

$$v_i = \frac{d(p_i, p_{i+1})}{\Delta t}$$

where $\Delta t$ is the time interval between two successive time points. The instantaneous speed is also the derivative of the traveled distance $D_t$.

Then the mean speed is calculated as the average of the instantaneous speed:

$$\bar{v} = \frac{1}{N-1} \sum_{i=1}^{N-1} v_i$$

The mean squared displacement is calculated as $$MSD(n) = \frac{1}{N} \frac{1}{n} \sum_{i=1}^{N-n} d^2(p_i, p_{i+n})$$

Bleach Correction

For several time-lapse datasets (FIGS. 8A-8H and FIGS. 9A-9F), the inventors performed standard bleaching correction using an ImageJ Plugin (Bleach Correction, https://imagej.net/Bleach_Correction) with the 'simple ratio' method.

Flat Fielding

Due to the spatially nonuniform profile of the excitation laser beam, the excitation intensity in both conventional- and the instant TIRF-SIM 100 is not distributed uniformly even when the excitation is scanned. The scanned excitation distribution has highest intensity in the center of the field of view and diminishes at increasing distances perpendicular to the scanning direction. In an attempt to normalize for this variation in excitation intensity ('flat fielding'), in some of the datasets (FIGS. 8A-8H, FIGS. 9A-9F, FIGS. 14A-14B, FIGS. 16A-16D, and FIGS. 17A-17B) the test averaged 100 images of a thin fluorescein layer, smoothed the average perpendicular to the scan direction, and divided the raw data by this smoothed average prior to deconvolution.

Sample Preparation

Fixed Samples

For imaging microtubules within fixed samples (FIGS. 7A-7E), high index coverslips were first immersed in 70% ethanol for ~1 min and allowed to air dry in a sterile cell culture hood. U2OS cells were grown on uncoated high index coverslips until ~50% confluency. The entire coverslip was submerged for 3 minutes in methanol pre-chilled to −20° C. to fix the cells. Coverslips were then washed in room temperature PBS extensively before blocking in antibody dilution buffer (Abdil; 1% BSA, 0.3% Triton-X 100 in PBS) for 1 hour at room temperature. The primary antibody stain was performed overnight at 4 degrees C. using 1/500 mg/ml of mouse anti alpha-Tubulin (Thermo Scientific #62204) in Abdil. The secondary antibody stain was performed for 1-2 hours at room temperature using 1/200 mg/ml of goat anti-mouse Alexa 488 (Invitrogen A11001) in Abdil.

Live Jurkat T Cells

High index coverslips were rinsed with 70% ethanol and dried with filtered air. The slides were then incubated in Poly-L-Lysine (PLL) at 0.01% WN (Sigma Aldrich, St. Louis, Mo.) for 10 min. PLL solution was aspirated and the coverslip was left to dry for 1 hour at 37° C. Coverslips were next incubated with streptavidin (Invitrogen) at 2 µg/ml for 1 hour at 37° C. and excess streptavidin washed with PBS. T cell activating antibody coating was performed by incubating the slides in a 10 µg/ml solution of biotin labeled anti-CD3 antibody (OKt3, eBiosciences, San Diego, Calif.) for 2 hours at 37° C. Excess antibody was removed by washing with L-15 imaging media immediately prior to the experiment. E6-1 Jurkat T-cells were transiently transfected with EMTB-3XGFP (FIGS. 8A and 8B) or F-tractin EGFP plasmid using the Neon (Thermofisher Scientific) electroporation system two days before the experiment. EMTB-3XGFP was a gift from William Bement (Addgene plasmid #26741) and pEGFP-C1 Ftractin-EGFP was a gift from Dyche Mullins (Addgene plasmid #58473).

Live U2OS Cells

Ras, Rab, VSVG, ER Imaging

Human osteosarcoma U2OS cells were routinely passaged in DMEM (Life technologies) plus 10% FBS (Hyclone) at 37° C., with 5% CO2. For cleaning prior to live cell imaging, high index coverslips were boiled for 5 minutes with distilled water, thoroughly rinsed with distilled water and stored in 90% ethanol for at least 2 hours. In order to facilitate cell adherence, the coverslips were coated with FBS for 2 hours at 37° C. The day prior to transfection, cells were plated on cleaned coverslips, at a density of ~60%. Cells were transfected with the appropriate plasmid using Turbofect (Life Technologies) at a ratio of 3:1 (Liposomes:DNA). The next day, the medium was replaced with fresh DMEM plus 10% FBS without phenol red, which was also used as the imaging medium. To monitor wild type Ras dynamics the inventors used EGFP-H-Ras (FIGS. 8C and 8D; FIGS. 15A and 15B), or if imaged with VSVG-GFP (Addgene #11912) (FIGS. 8E-8G; FIGS. 15A and 15B), the test used a HaloTag chimera of H-Ras (gift of Dominic Esposito, NCI). Halotag proteins were labeled using Janelia Fluor549 (kind gift of Luke Lavis, Janelia Research Campus) at a final concentration of 100 nM for 15 minutes. Following labelling, the cells were rinsed twice with plain DMEM, incubated with fresh medium plus 10% FBS for 20 minutes, and finally the medium replaced with fresh, phenol red free DMEM plus 10% FBS. The dynamics of Rab GTPase was followed for GFP tagged Rab11 Addgene #12674)(FIGS. 9A-9F; FIGS. 15A-15B, and FIGS. 16A-16D). For dual labelling of Ras and the endoplasmic reticulum, the inventors co-transfected the GFP-H-Ras construct with pDsRed2-ER (Clontech, cat #632409) (FIGS. 8H and 8I), which carries a KDEL ER retention signal.

Myosin Imaging

For imaging moysin IIA (FIG. 14A), high index coverslips were plasma cleaned (PDC-001, Harrick Plasma) for 5 minutes, and then coated with 10 µg/ml human plasma fibronectin (Millipore, cat. # FC010) in PBS (ThermoFisher). U2OS cells were cultured in McCoys media (Invitrogen) supplemented with 10% fetal calf serum (ThermoFisher), at 37° C. in 5% $CO_2$. Cells were transfected with GFP-myosin IIA expression and mApple-F-tractin plasmids as previously described and cultured for 12 hours prior to plating on fibronectin coated coverslips.

Actin Imaging

For actin imaging, U2OS cells were cultured at 37° C. in the presence of 5% CO2 in high glucose DMEM medium (ThermoFisher) with 10% fetal bovine serum, 1% Pen/Strep and GlutaMAX™ (ThermoFisher). Cells were seeded on high index coverslips and transfected with Lifeact.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for structured illumination microscopy comprising:
   a light source for generating an excitation light beam;
   a first micro lens array for splitting the excitation beam into an array of excitation foci;
   a first lens aligned along the first axis and positioned one focal length away from a focal point of the first micro lens array, the first lens focusing the array of excitation foci;

a radial aperture block aligned along the first axis positioned at a front focal plane of the first lens, the radial aperture block being configured to block a plurality of low-angle central rays of the array of excitation foci, while allowing a plurality of high-angle, marginal rays of the array of excitation foci to pass through the radial aperture block, wherein the high-angle marginal rays are focused by the first lens along a high-angle and low-angle central rays are focused by the first lens along a low-angle;

a galvanometric mirror aligned and positioned for redirecting and scanning the high-angle, marginal rays through an objective lens for focusing the redirected high-angle, marginal rays along a sample that generates an excitation by the sample and then the excitation from the sample is rescanned to generate a patterned fluorescence emissions onto a second microlens array for locally contracting the patterned fluorescence emissions into a contracted pattern of fluorescence emissions; and a mirror arrangement for redirecting the contacted patterned fluorescence emissions onto a detector for detecting the patterned fluorescence emissions emitted by the sample.

2. The system of claim 1, further comprising:
a second lens and a third lens positioned between the radial aperture block and the dichroic mirror, wherein the second and third lenses collectively image the high angle, marginal rays onto the galvanometric mirror.

3. The system of claim 1, wherein the high-angle marginal rays evanescently excite the sample.

4. The system of claim 1, wherein the radial aperture block is positioned at a plane conjugate to the back focal plane of the objective lens.

5. The system of claim 1, wherein the patterned fluorescence emissions are descanned by the galvanometric mirror.

6. The system of claim 1, wherein the second microlens array has the same pitch/pattern and lens spacing as the first microlens array.

7. The system of claim 1, further comprising:
a dichroic mirror in communication with the first microlens array, the galvanometric mirror, and second microlens array for allowing the high angle, marginal rays to pass directly through the dichroic mirror or allowing the patterned fluorescence emissions to be redirected from the galvanometric mirror to the second microlens array.

8. The system of claim 1, wherein an emission filter is positioned between the pair of mirrors and the galvanometric mirror for removing any residual excitation from the contracted patterned fluorescence emissions prior to detection by the detector.

9. The system of claim 1, wherein the local contraction of the patterned fluorescence emissions is based on a contraction factor set by the respective wavelengths of the excitation beam and the patterned fluorescence emissions and the physical characteristics of the radial aperture block.

10. The system of claim 1 wherein the contraction factor is set at a value of approximately 2.

11. A system for structure illumination microscopy comprising:
a light source for generating an excitation light beam;
a first micro-lens array for splitting the excitation beam into an array of excitation foci;
a first lens aligned along the first axis and positioned one focal length away from a focal point of the first micro-lens array, the first lens focusing the array of excitation foci;
a digital micro-mirror device positioned at a front focal plane of the first lens, the digital micro-mirror device being operable to reflect a plurality of low-angle central rays of the array of excitation foci off axis relative to an axis defined by the digital micro-mirror device such that only high-angle marginal rays that are focused by the first lens along a high-angle are not reflected by the digital micro-mirror device;
a galvanometric mirror positioned for redirecting and scanning the high-angle, marginal rays through an objective lens for focusing the redirected high-angle, marginal rays along a sample that generates an excitation by the sample and then the excitation from the sample is rescanned by the galvanometric mirror to generate a patterned fluorescence emissions onto a second microlens array for locally contracting the patterned fluorescence emissions into a contracted patterned fluorescence emissions; and
a mirror arrangement for redirecting the contacted patterned fluorescence emissions onto a detector for detecting the patterned fluorescence emissions emitted by the sample.

12. The system of claim 1, wherein the digital micro-mirror device comprises a plurality of pixels and wherein the digital micro-mirror device is operable such that a number of the plurality of pixels are set to establish a reflective zone that reflect the low-angle central rays off axis.

13. The system of claim 12, wherein the number and location of the plurality of pixels in the reflective zone is varied such that the thickness of an evanescent field at the sample is also varied.

14. The system of claim 11, wherein the galvanometric mirror scans the high-angle marginal rays onto a back focal plane of an objective lens that produces a structured illumination that evanescently excites the sample.

15. The system of claim 14, wherein the objective lens has a numerical aperture of greater than 1.4 (or the refractive index of the sample).

16. A system for structured illumination microscopy comprising:
a light source for generating an excitation light beam;
a spatial light modulator for controlling the phase of the excitation beam for generating an array of excitation foci with minimal interference between each excitation foci;
a first lens positioned one focal length away from a focal point of the spatial light modulator, the first lens focusing the array of excitation foci;
a radial aperture block aligned along the first axis positioned at a front focal plane of the first lens, the radial aperture block being configured to block a plurality of low-angle central rays of the array of excitation foci, while allowing a plurality of high-angle, marginal rays of the array of excitation foci to pass through the radial aperture block, wherein the high-angle marginal rays are focused by the first lens along a high-angle and low-angle central rays are focused by the first lens along a low-angle;
a galvanometric mirror aligned and positioned for redirecting and scanning the high-angle, marginal rays through an objective lens for focusing the redirected high-angle, marginal rays along a sample that generates an excitation by the sample and then the excitation from the sample is rescanned to generate a patterned fluorescence emissions onto a microlens array for locally contracting the patterned fluorescence emissions into a contracted patterned fluorescence emissions; and a mirror arrangement for redirecting the contracted patterned fluorescence emissions onto a detector for detecting the patterned fluorescence emissions emitted by the sample.

17. The system of claim 16, wherein the radial aperture block is positioned at a plane conjugate to the back focal plane of the objective lens.

18. The system of claim 16, wherein the spatial light modulator is operable to split the excitation beam into an array of excitation foci.

19. The system of claim 16, further comprising:
a telescopic arrangement comprising a second lens in line with a third lens to collectively image the high-angle marginal rays that pass through the radial aperture block onto the galvometric mirror.

20. The system of claim 16, wherein high-angle marginal rays impinge upon the sample at an angle that exceeds the critical angle the high-angle marginal rays do not propagate into the sample causing only an evanescent wave to be produced that decays exponentially within the sample.

* * * * *